United States Patent [19]
Loike et al.

[11] Patent Number: 5,843,436
[45] Date of Patent: Dec. 1, 1998

[54] METHOD OF PREVENTING AND TREATING BACTERIAL INFECTION OF SUTURES AND PROSTHETIC DEVICES, AND PROMOTING INGRESS OF LEUKOCYTES INTO TUMOR FOCI

[75] Inventors: John Loike, Jamaica Estates; Samuel C. Silverstein, New York, both of N.Y.

[73] Assignee: The Trustees of Columbia University, in the City of New York, New York, N.Y.

[21] Appl. No.: 635,572

[22] Filed: Apr. 22, 1996

[51] Int. Cl.$^6$ .......................... A61K 38/49; A61K 38/14; A61F 2/02; A61F 4/00
[52] U.S. Cl. .................. 434/94.64; 24/423; 24/94.63; 24/532; 514/2
[58] Field of Search ........................ 514/2; 424/94.63, 424/94.64, 532, 423

[56] References Cited

PUBLICATIONS

Nakamoto et al Investigative Radiology vol. 30: 341–344, (1995) Jun.

Goodman & Gilman Chapter 58 The Pharmacological Basis of Therapeutics p. 1362.

Bourdon, M.A., Ruoslahti, E. (1989). Tenascin mediates cell attachment through an RGD–dependent receptor. J. Cell Biology 108:1149–1155.

Chiquet–Ehrismann, R. (1993). Tenascin and other adhesion–modulating proteins in cancer. [Review]. Sem. in Cancer Biol. 4:301–10.

Downey, G.P. (1994). Mechanisms of leukocyte motility and chemotaxis. Current Opinion in Immunol. 6:113–124.

El Khoury, J., Loike, J.,, Cao, L., Thomas, C. and Silverstein, S.C. (1994). Macrophages adhere to glucose–modified basement membrane collagen via their scavenger receptors. J. Biol. Chem. 269:10197–10200.

Friedlander, D.R., Hoffman, S., and Edelman, G.M. (1988). Functional mapping of cytotactin: proteolytic fragments active in cell–substrate adhesion. J. Cell Biol. 107:2329.

Furie M.B., Naperstek, B.L., and Silverstein, S.C. (1987). Migration of neutrophilis across monolayers of cultured mocrovascular endothlial cells. An in vitro model of leucocyte extravasation. J. Cell. Sci. 88:161–175.

Gao, J.X., Wilkins, J., and Issekutz, A.C. (1995). Migration of human polymorphonuclear leukocytes through a synovial fibroblast barrier is mediated by both beta 2 (CD11/CD18) integrins and the beta 1 (CD29) integrins VLA–5 and VLA–6. Cell Immunol. 163:178.

Goodman, S.L., Risse, G., and von der Mark, K. (1989). The E8 subfragment of laminin promotes locomotion of myoblasts over extracellular matrix. J. Cell. Biol. 109:799–809.

Gresham, H.D., Graham, I.L., Anderson, D.C., and Brown, E.J. (1991) Leukocyte adhesion–deficient neutrophils fail to amplify phagocytic function in response to stimulation. Evidence for CD11b/CD18–dependent and –independent mechanisms of phagocytosis. J. Clin. Invest. 88:588.

Joshi, P., Chung, C.Y. Aukil, I., and Erickson, H.P. (1993). Endothelial cells adhere to the RGD domain and the fibrinogen–like terminal knob of tenascin. J. Cell Sci. 106:389–400.

Klemke, R.L., Yebra, M., Bayna, E.M., and Cherish, D.A. (1994). $\alpha v \beta 5$ directed cell mobility but not adhesion on vitronectin. J. Cell Biol. 127:859–866.

Koukouus, G.K., Gould, V.E., Bhattacharyya, A., Gould, J.E., Howeedy, A.A., and Virtanen, I. (1991). Tenascin in normal, reactive, hyperplastic and neoplastic tissue: biological and pathological implications. Hum. Pathol. 22:636.

Lanir, N., Ciano, P.S., Van De Water, L., Mcdnagh, J., Dvorak, A.N., and Dvorak, H.P. (1988). Macrophage migration in fibrin gel matrices. II. Effects of clotting factor XIII, fibronectin, and glycosaminoglycan content on cell migration. J. Immunol. 140:2340–2349.

Loike, J.D., Cao, L. and Silverstein, S.C. (1995). integrins regulate the chemotaxis of FMLP–Stimulated neutrophils through fibrin gels.

Molecular Biology of the Cell, 6:284a;abstract 1650.

Loike, J.D., El Khoury, J., Cao, L., Richards, C.P., Rascoff, H., Mandevill, J.T.H., Maxfield, F.R., and Silverstein, S.C. (1995).

Fibrin Regulates Neutrophil Migration in Response to Interleukin 8, Leukotriene B4, Tumor Necrosis Factor, and Formyl–Methionyl–121:945–955.

Loike, J.D., Sodeik, B., Cao, L., Leucona, S., Weitz, J.I., Detmers P.A., Wright, S.D., and Silverstein S.C. (1991). CD11c/CD18 on Neutrophils recognizes a domain at the N terminus of the A of fibrinogen. Proc. Natl. Acad. Sci., 88:1044–1048.

Leucyl–Phenylalanin. J. Exp. Med. 1763–1772.

Loike, J.D., Silverstein, R., Cao, L., Solomon, L., Weitz, J.I., Haber, E., Matsueda, G.R., Bernatowicz, M.S., and Silverstein, S.C. (1993). Activated platelets form protected zones of adhesion with fibrinogen and fibronectin–coated surfaces. J. Cell Biol., 121:945–955.

Lundgren–Akerlund, E., Olofsson, A.M., Bergerand, E., and Arfors, K.E. (1993). CD11b/CD18–dependent polymorphonuclear leucocyte interaction with matrix proteins in adhesion and migration. Scan. J. Immunol. 37:569.

Mackie., E.J., Halfter, W., and Liverani, D. (1988). J. Cell Biol. 107:2757–2767.

(List continued on next page.)

*Primary Examiner*—Lila Feisee
*Assistant Examiner*—Geetha P. Bansal
*Attorney, Agent, or Firm*—John P. White; Cooper & Dunham LLP

[57] ABSTRACT

An agent capable of inhibiting signalling mediated by a $\beta_1$ integrin cell surface receptor of leukocyte cells will treat a bacterial infection associated with a surface of a foreign body over and around which fibrin has been deposited, or a malignant tumor over and around which tenascin has been deposited. In addition, coating a foreign body with a fibrinolytic agent will prevent chronic bacterial infection associated with the surface of the foreign body. Furthermore, an agent capable of stimulating signalling mediated by a $\beta_1$ integrin cell surface receptor of leukocyte cells will treat chronic inflammation.

10 Claims, 19 Drawing Sheets

OTHER PUBLICATIONS

Mackie, E.J., Chiquet–Ehrismann, R., Pearson, C.A., Inaguma, Y.M., Taya, K., Kawarada, Y., and Sakakura, T. (1987). Proc. Natl. Acad. Sci. 84:4621–4625.

Monboisse, J–C., Garnotel, R., Bellon, G., Ohno, N., Perreau, C, Borel, J.P., and Kefalides. (1994). The α3 chain of type IV collagen prevents activation of human polymorphonuclear leukocytes. J. Biol. Chem. 269:25475–25482.

Pesheva, P., Probstmeier, R., Skubitz, A.P., McCarthy, J.B., Furcht, L.T. and Schachner, M. (1994). Tenascin–R J1 160/180 inhibits fibronectin–mediated cell adhesion—functional relatedness to tenascin–C. J. Cell Sci. 107:2323–33.

Prieto, A.L., Edelman, G.M., and Crossin, K.L. (1993). Multiple integrins mediate cell attachment to cytotactin/tenascin. Proc. Natl. Acad. Sci. USA 90:10154–8.

Ruegg, C.R., Chiquet–Ehrismann, R., and Alkan, S.S. (1989). Tenascin, and extracellular matrix protein, exerts immunomodulatroy activities. Pro. Natl. Acad. Sci. 86:7637–7441.

Schmidt, A.M., Yan, S.D., Brett, J., Mora, R., Nowygrod, R., and Stern, D. (1993). Regulation of human mononuclear phagocyte migration by cell surface–binding proteins for advanced glycation end products. J. Clin. Invest. 91:2155.

Sharifi, B.G., D.W. Lafleur, S.M. Schwartz, J.S. Forrester, J.A., Fagin. (1995). Expression of tenascin isoforms are selectively up–regulated following aortic balloon. The FASEB Journal, 9:a611.

Sriramarao, P., Mendler, M., and Bourdon, M.A. (1993). Endothelial cell attachment and spreading on human tenascin is mediated by alpha v beta 3 integrins. J. Cell Sci. 105:1001–12.

Thompson, H.L., and Matsushima, K. (1992). Human polymorphonuclear leucocytes stimulated by TNF–α show increased adherence to extracellular matrix proteins which is meediated via the CD11b/18 complex. Clin. Exp. Immunol. 90:280–285.

Wehrle–Haller, B. and Chiquet, M. (1993). Dual function of tenascin: simultaneous promotion of neurite growth and inhibition of glial migration. J. Cell Sci. 106:597–610.

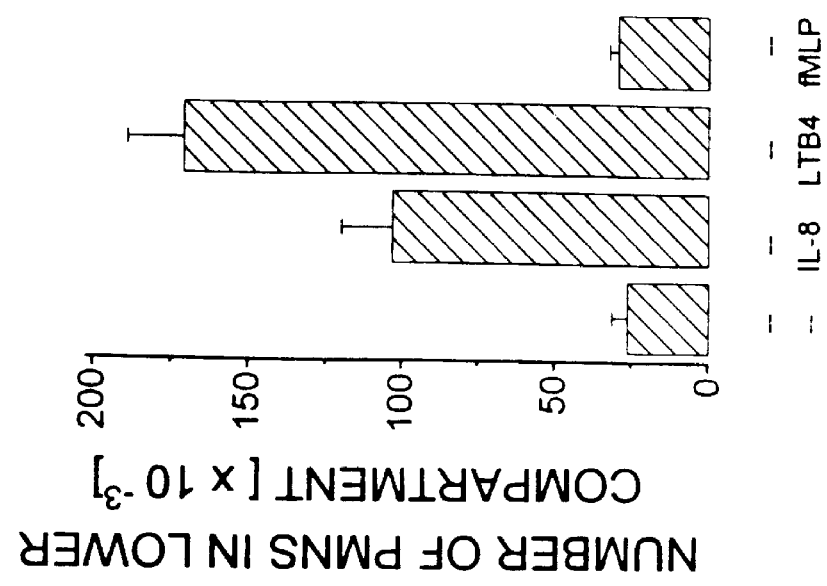
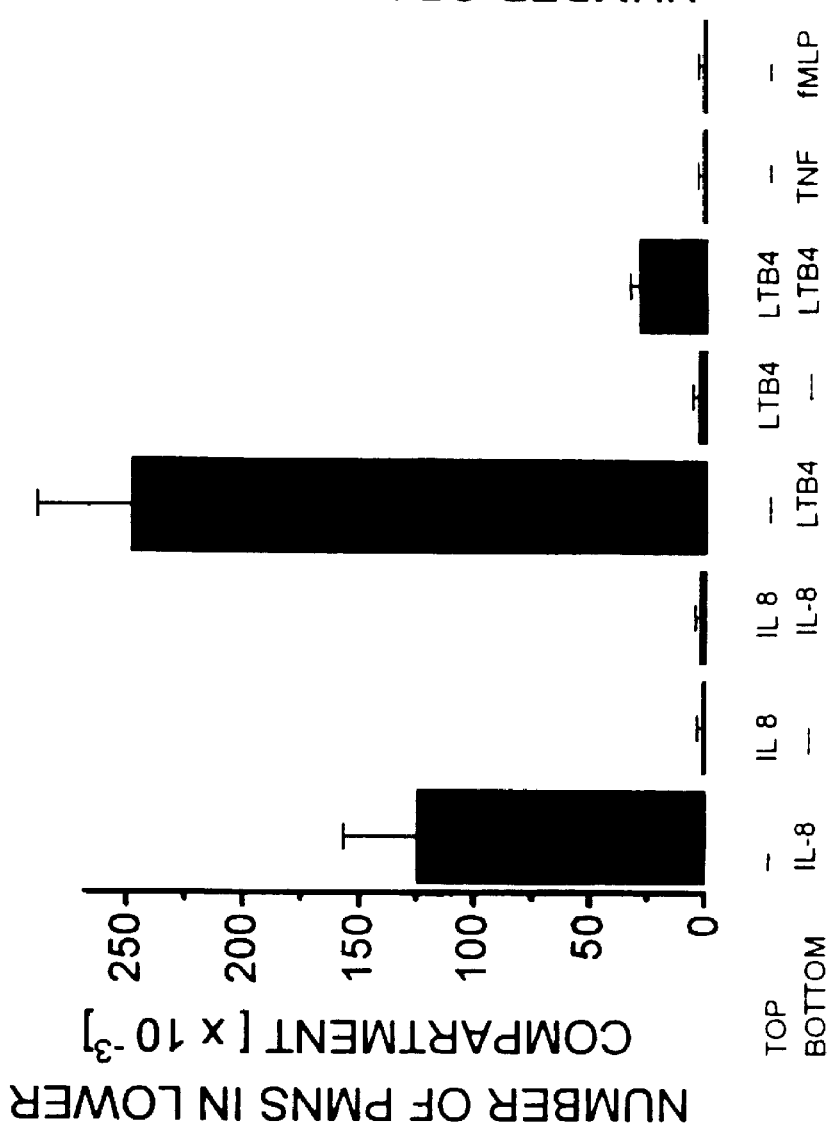

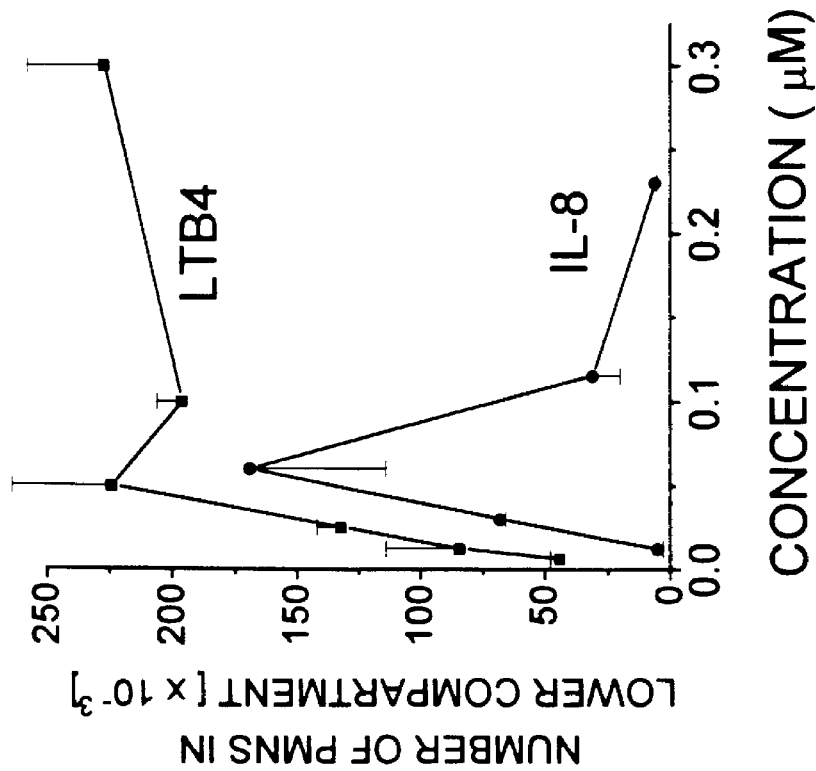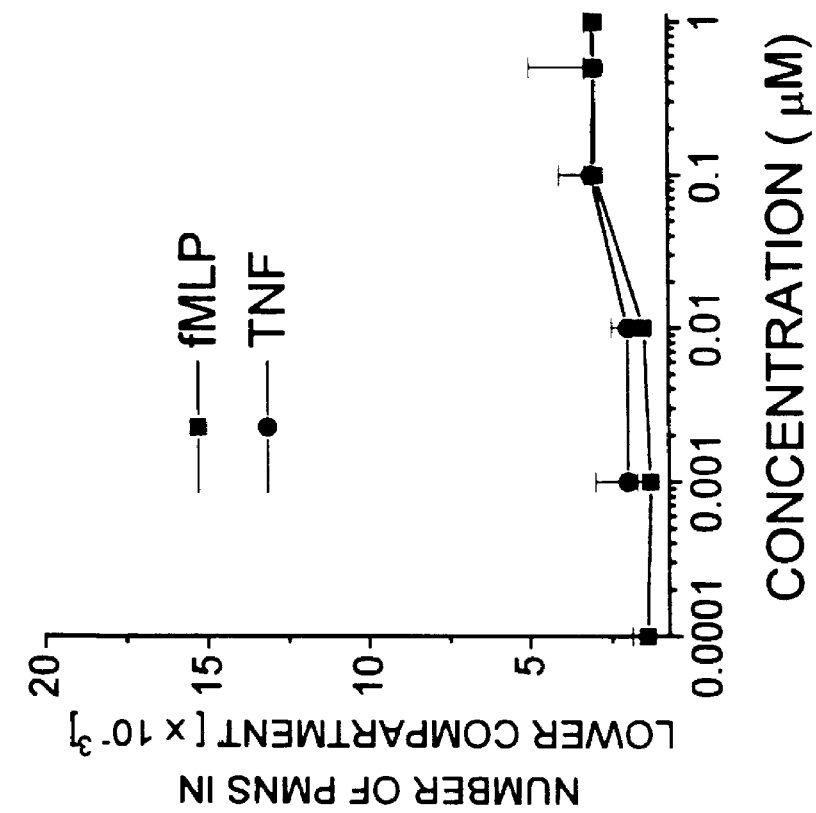

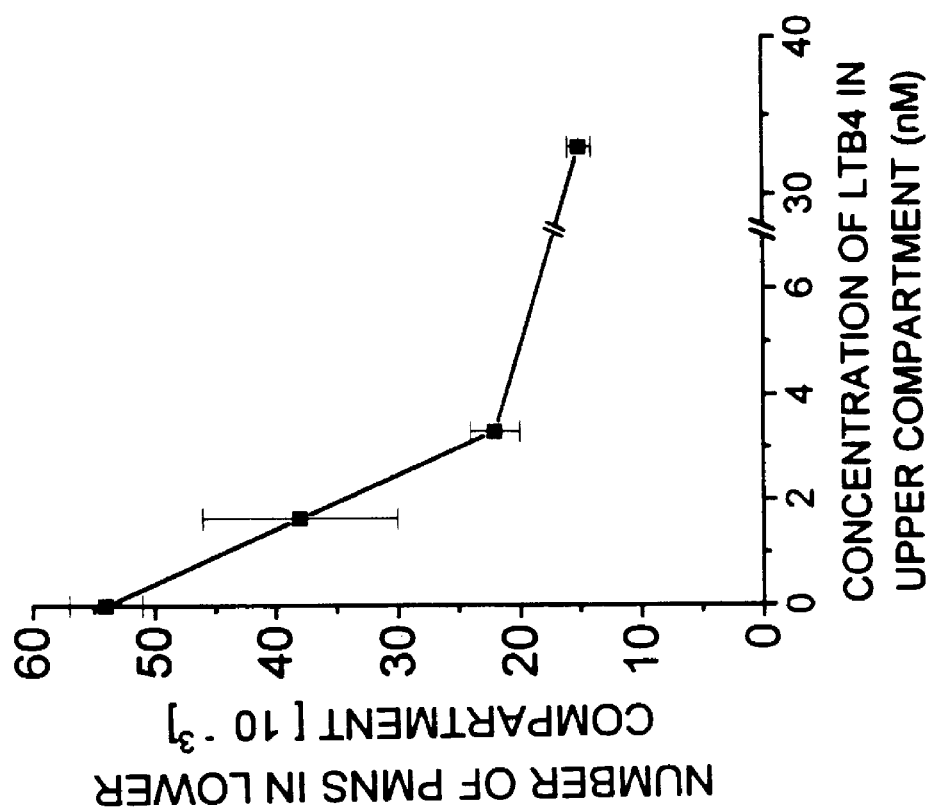
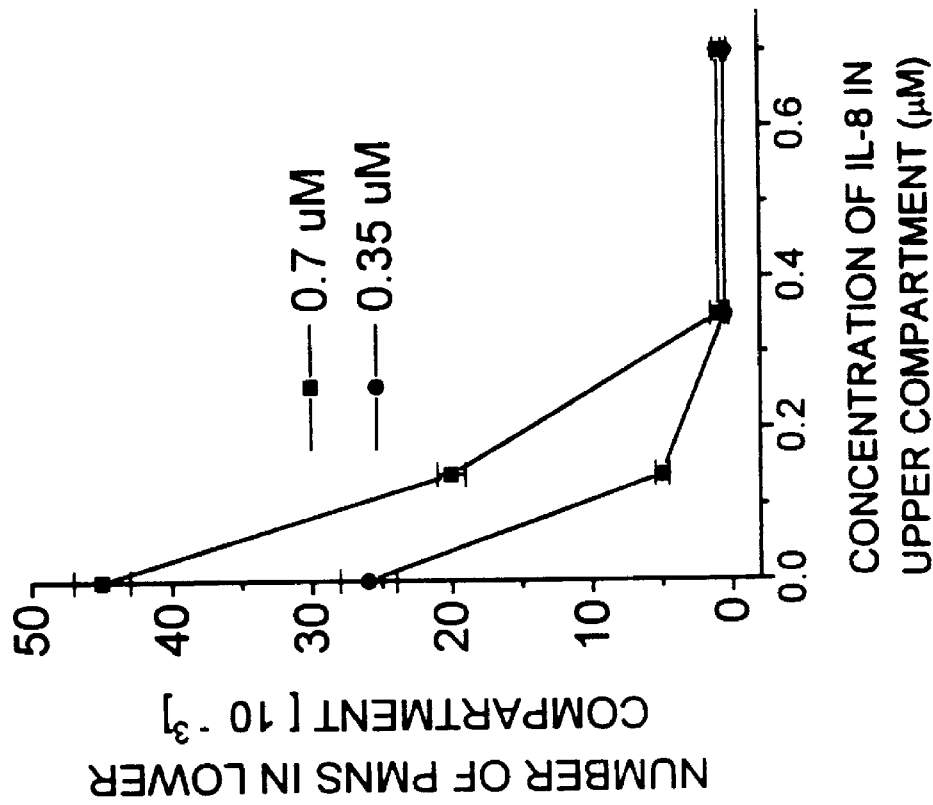

FIG. 5A  
1 h
FIG. 5B  
4 h
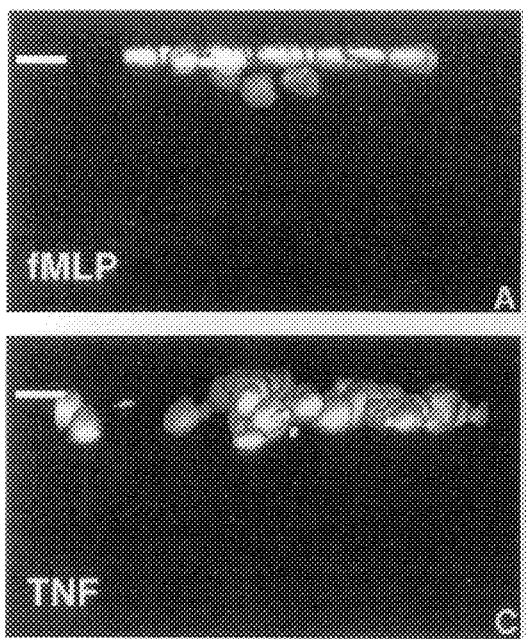
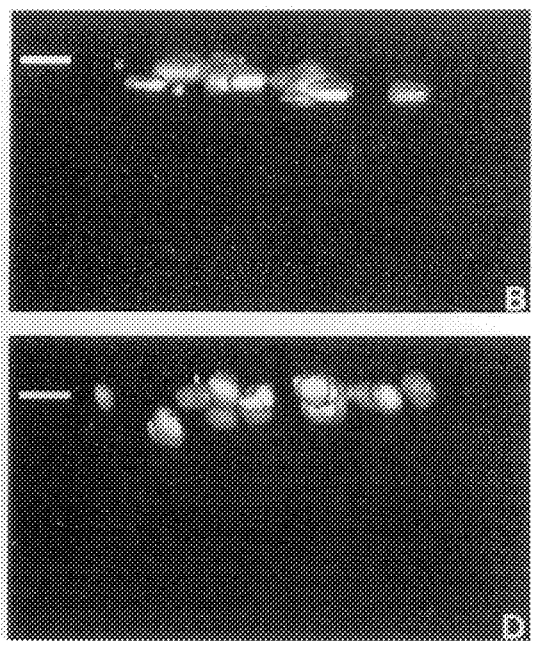
FIG. 5C
FIG. 5D 1 h

4h

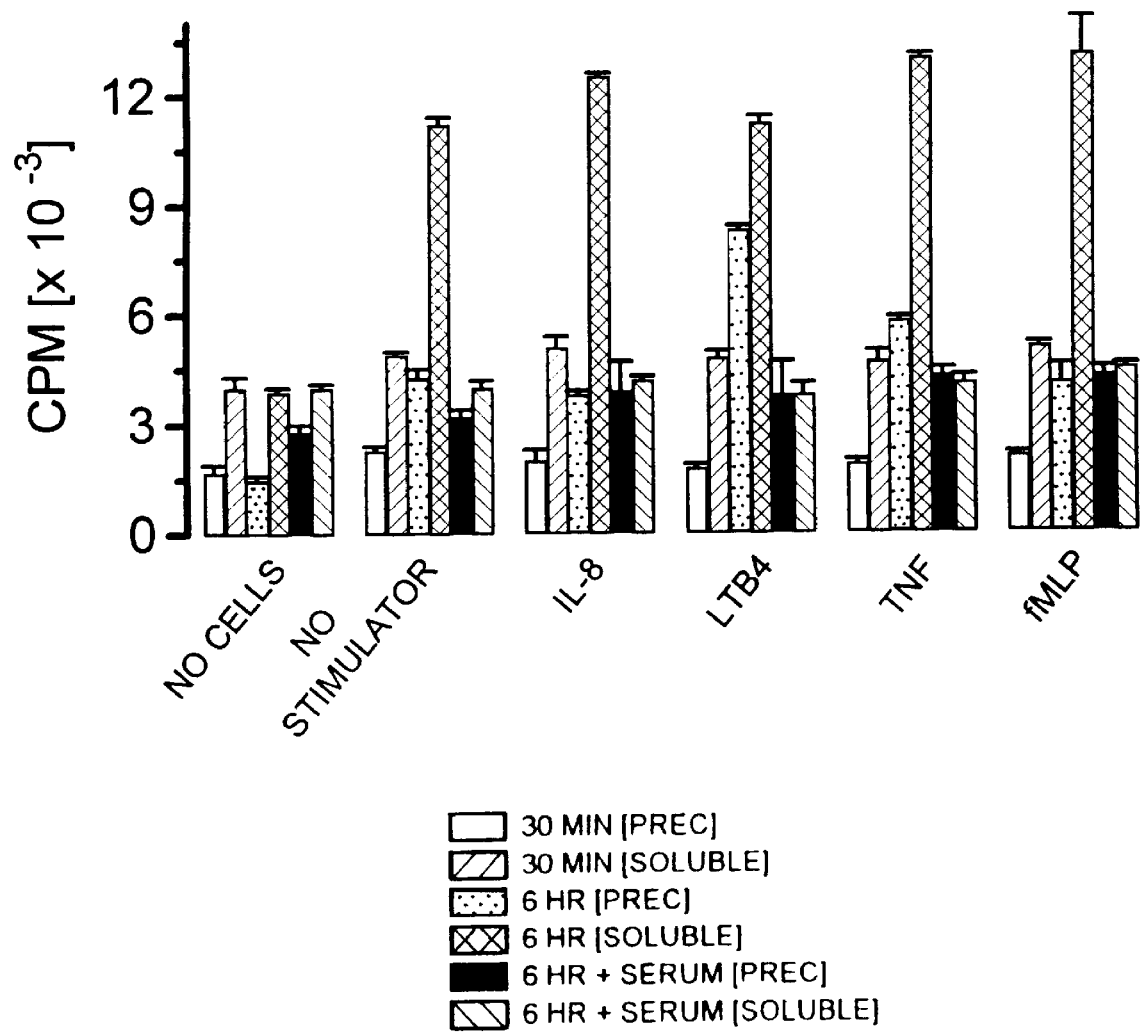

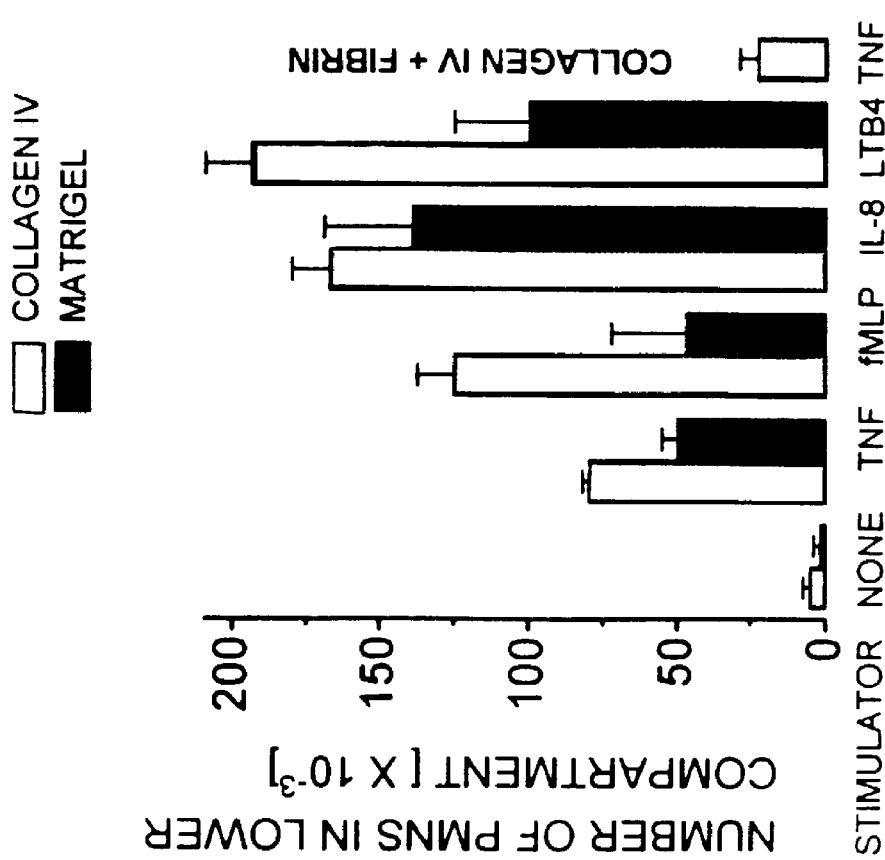
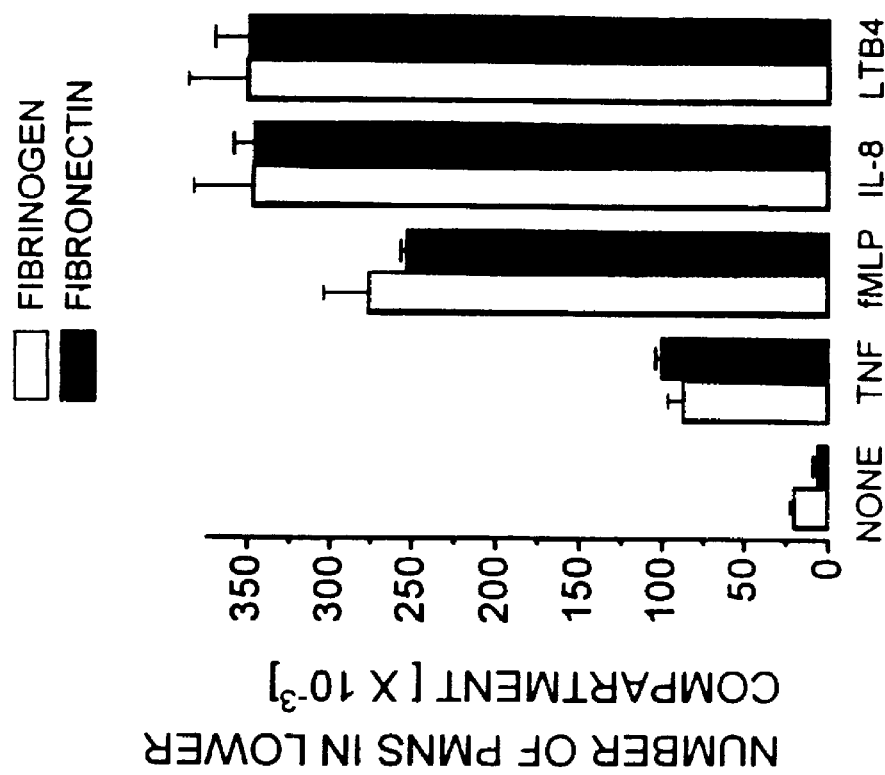

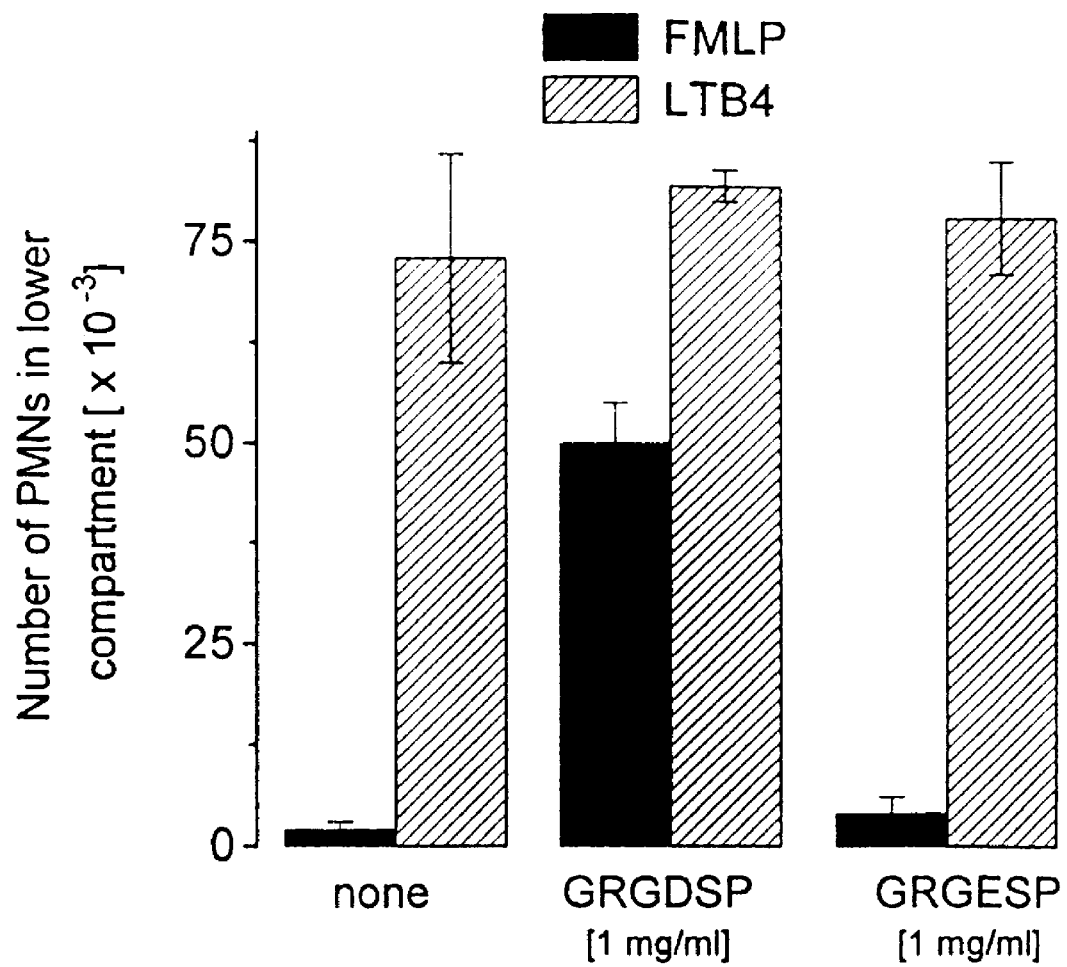

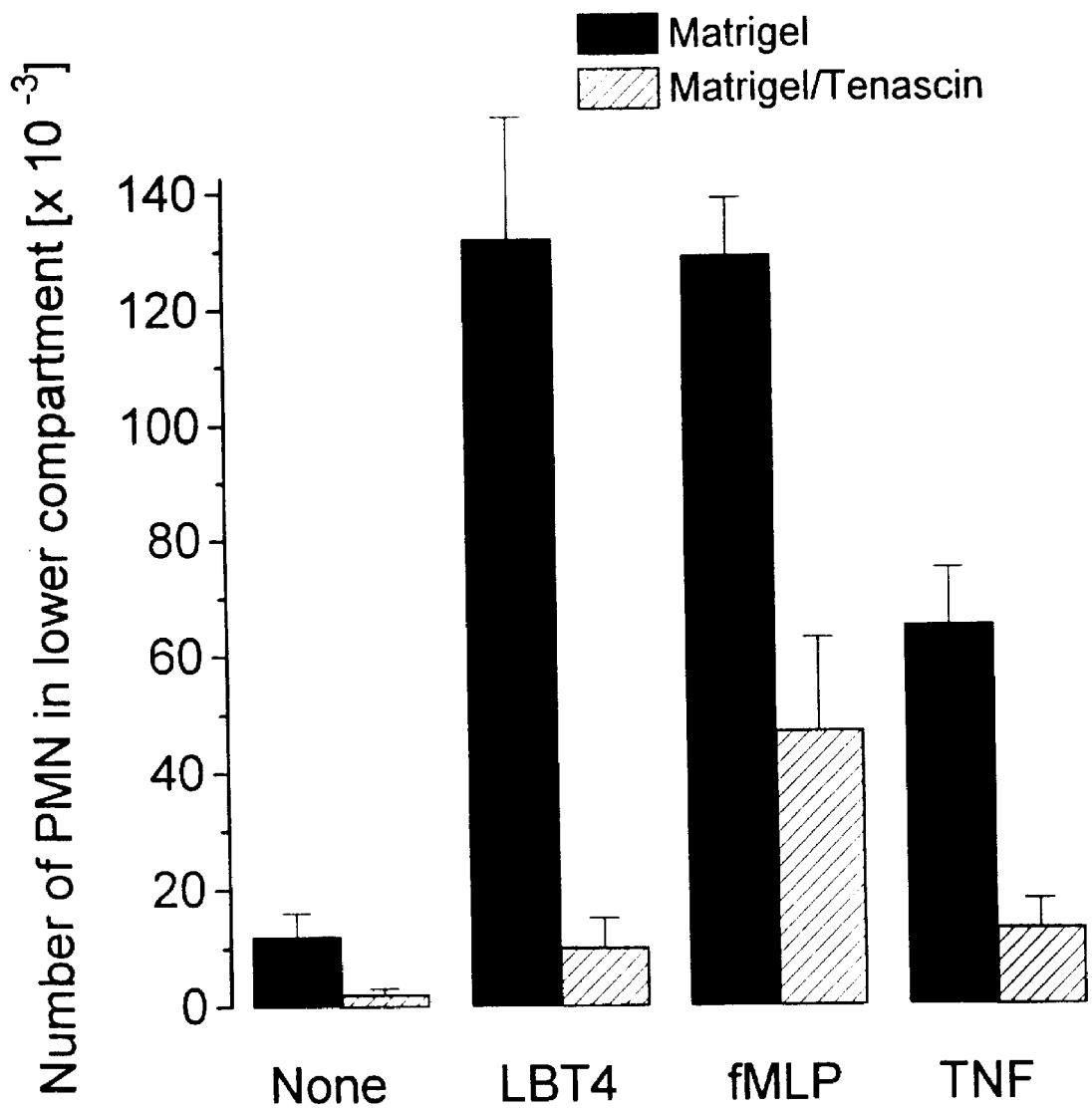

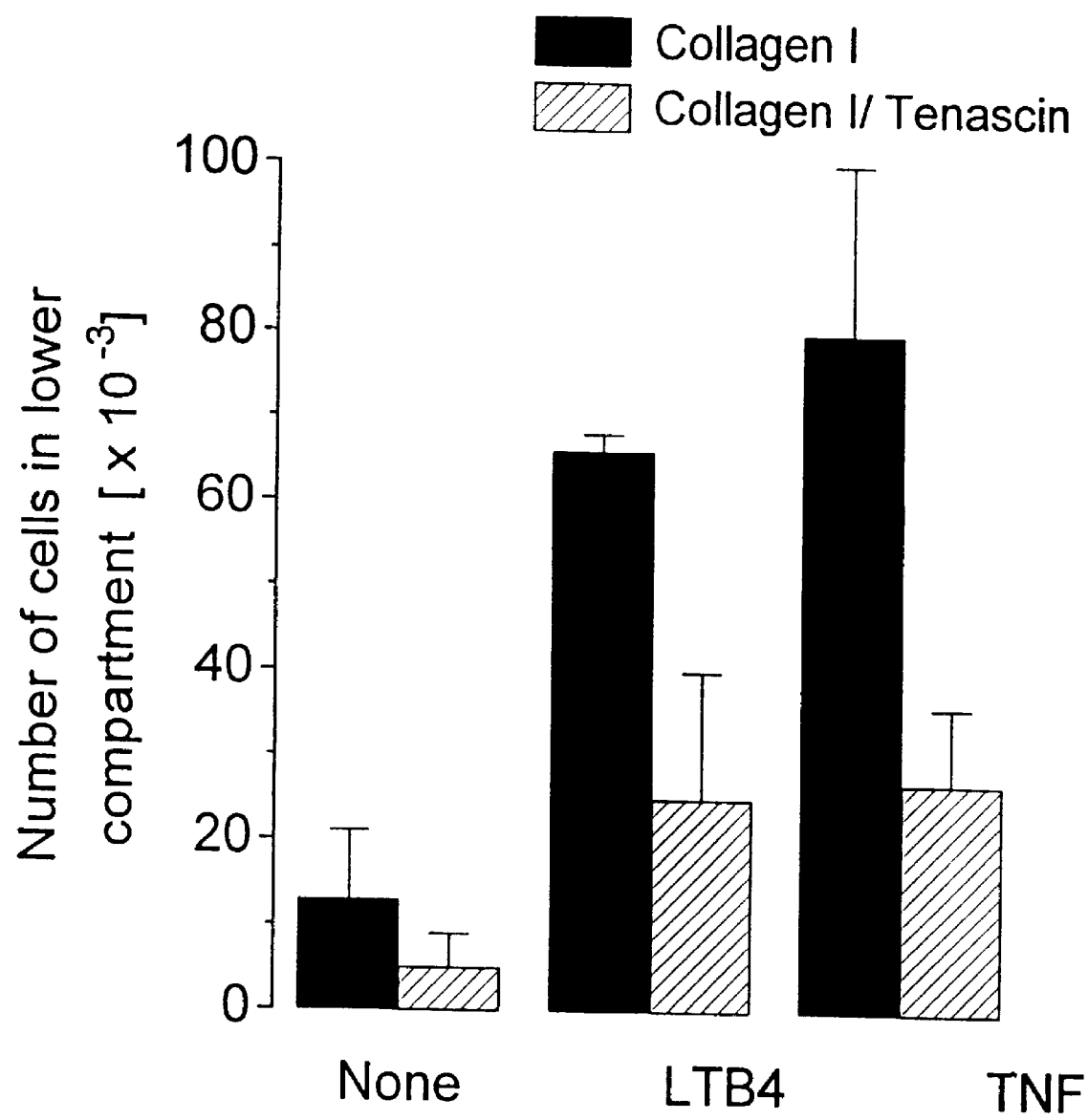

METHOD OF PREVENTING AND TREATING BACTERIAL INFECTION OF SUTURES AND PROSTHETIC DEVICES, AND PROMOTING INGRESS OF LEUKOCYTES INTO TUMOR FOCI

The invention disclosed herein was made with Government support under NIH Grant No. AI 20516 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

BACKGROUND OF THE INVENTION

Soluble or cell bound chemoattractants (1,2), stimulate polymorphonuclear leukocytes (PMN) to emigrate from the vasculature and migrate toward sites of injury, infection, and inflammation. PMNs express unique plasma membrane receptors for many different chemoattractants and cytokines [e.g., IL-8, leukotriene B4 (LTB4), formyl-methionyl-leucyl-phenylalanine (fMLP) and TNF-$\alpha$] (3). Interactions between these receptors and soluble or surface-bound chemoattractants or cytokines signal PMNs to alter their expression and/or activity of selectins and integrins (4,5), and regulate PMN spatial orientation and movements. (6).

Tenascin, also referred to as cytotactin, hexabrachion, and glioma-mesenchymal extracellular matrix protein (41,43, 44), forms a disulfide linked multimeric six-armed structure called a hexabrachion (43). Tenascin is expressed in many tissues during embryonic development, and is thought to play an important role in the development of muscles and tendons, mammary glands, hair follicles, teeth, kidney, bone and cartilage (43,50,51). In adults, tenascin is expressed in T-cell dependent regions of lymphoid tissues (40), in areas of cellular injury, and in malignant but not benign tumors (41,43). In areas of injury, tenascin is present in granulation tissue (41,55), in association with proliferating and migrating epidermal cells (42,49), and in arteries whose endothelial cells have been damaged (57). In malignant neoplasms, tenascin is produced by the tumor cells (63) and deposited in the stroma of gliomas, mammary carcinomas, colon cancers, Wilm's tumor, basal cell carcinomas, melanomas, and squamous cell carcinomas (41,64).

There is little information regarding the physiological or patho-physiological role(s) of tenascin at sites of tissue injury, malignancy or atherosclerotic lesions. In extracellular matrices, tenascin promotes the adhesion of endothelial cells and bone marrow cells (38,48). Tenascin also blocks the attachment of several other cell types to fibronectin-coated surfaces in vitro (47,52), and the migration of neural crest cells (20,43,62).

SUMMARY OF THE INVENTION

The present invention provides a method of treating an infection caused by bacterial cells located on a surface of a foreign body over and around which fibrin has been deposited, the foreign body being present in a subject, which comprises administering to the subject an agent capable of inhibiting signalling mediated by a $\beta_1$ integrin cell surface receptor of leukocyte cells in an amount effective to enhance the migration of leukocyte cells into or through the fibrin so as to permit the leukocyte cells to reach and kill the bacterial cells and thereby treat the infection.

The present invention also provides a method of preventing a chronic infection from occurring due to the presence of bacterial cells on a surface of a foreign body in a subject, which comprises coating the foreign body before placing it in the subject with a fibrinolytic agent capable of preventing the accumulation of fibrin on the surface of the foreign body so as to permit leukocyte cells to reach and kill any bacterial cells present on the surface of the foreign body and thereby prevent the chronic infection.

The present invention further provides a method of treating a malignant tumor comprising of malignant tumor cells over and around which tenascin has been deposited, the malignant tumor being present in a subject, which comprises administering to the subject an agent capable of inhibiting signalling mediated by a $\beta_1$ integrin cell surface receptor of leukocyte cells in an amount effective to enhance the migration of leukocyte cells through the tenascin so as to permit the leukocyte cells to reach and kill the malignant tumor cells and thereby treat the malignant tumor.

The present invention also provides a method of treating a chronic inflammation in a subject caused by an increase in the number of leukocyte cells present at the site of the chronic inflammation which comprises administering to the subject an agent capable of stimulating signalling mediated by a $\beta_1$ integrin cell surface receptor of leukocyte cells in an amount effective to inhibit the migration of leukocyte cells toward the site of the chronic inflammation so as to reduce the number of leukocyte cells present at the site and thereby treat the chronic inflammation.

BRIEF DESCRIPTION OF THE FIGURES

FIGS. 1A and 1B show that IL-8 and LTB4 promote PMN migration through fibrin gels and plasma clots. Fibrin gels (A) or plasma clots (B) were formed on top of filters with 8 $\mu$m pores in tissue culture inserts as described under Materials and Methods. $10^6$ PMNs were added to the upper chamber and the indicated chemoattractants or cytokines were added to either the lower or upper chamber as indicated. The preparation then was incubated at 37° C. for 6 hrs, at which time the number of cells in the lower chamber was determined using a Coulter counter. Concentrations of chemoattractants/cytokines used were: $0.75\times10^{-7}$M for IL-8, $1.0\times10^{-7}$M for LTB4, $0.5\times10^{-7}$M for TNF and $1.0\times10^{-7}$M for fMLP. Fewer than 1500 PMNs migrated through fibrin gels in the absence of any stimulator.

FIGS. 2A and 2B show PMN migration through fibrin gels in response to varying concentrations of chemoattractants [fMLP, TNF (A); LTB4, IL-8 (B)]. Fibrin gels were formed on filters of cell culture inserts as described in Experimental Procedures and chemoattractants or cytokines at the indicated concentrations were added to the lower chamber. $10^6$ PMNs were added to the upper chamber and the preparation was incubated at 37° C. for 6 hrs, at which time the number of cells in the lower chamber was counted as described in FIGS. 1A and 1B.

FIGS. 3A and 3B show that an IL-8 or LTB4 gradient is required for PMN migration through fibrin gels. Fibrin gels were formed in cell culture inserts as described in Experimental Procedures. IL-8 (A) or LTB4 (B) were added to the lower compartment at a fixed concentration and to the upper compartment at varying concentrations as indicated. $10^6$ PMNs were added to the upper chamber and the preparation was incubated at 37° C. for 6 hrs, at which time the number of cells in the lower chamber was counted as described in FIGS. 1A and 1B.

FIGS. 5A, 5B, 5C, 5D, 5E, and 5F show a confocal microscopic analysis of PMN migration through fibrin gels. Fibrin gels were formed as described under Experimental Procedures and chemoattractants or cytokines at the indicated concentrations were added to the lower chamber. $10^6$ PMNs, prelabeled with Calcein as described under Experimental Procedures, were added to the upper chamber at 37° C. At the indicated times, the filters were removed from the inserts, washed and viewed by confocal microscopy as described under Experimental Procedures. All samples were viewed en-face, the images were rotated 90° C. The surface of the gel is marked with a bar. (A and B), fMLP ($10^{-7}$M); (C and D), TNF ($0.5 \times 10^{-7}$M); (E and F), IL-8 ($0.75 \times 10^{-7}$M).

FIG. 6 shows that degradation of $^{125}$I-fibrin by PMNs does not account for the increase of IL-8 of LTB4 stimulated PMNs. Cell culture inserts containing $^{125}$I-labeled fibrin gels were prepared as described. $10^6$ PMNs were added to the insert and the indicated chemoattractants/cytokine were added to the lower compartment as described in FIGS. 1A and 1B. The concentrations of chemoattractants used are the same as described in FIGS. 5A, 5B, 5C, 5D, 5E, and 5F.

After a 6 hr incubation at 37°, the media from both the upper and lower compartments were collected and assayed for the amount of radioactivity in TCA-soluble and insoluble fractions as described in Materials and Methods. This figure is representative of experiments repeated three times with similar results. The data in this figure are the average of values from duplicate samples.

FIGS. 7A and 7B show PMN migration through filters coated with different types of matrix proteins. PMN migration through filters coated with gels formed with reconstituted basement membrane (Matrigel), or collagen IV (A), or with filters coated with fibrinogen, or fibronectin (B), was measured in response to TNF ($5 \times 10^{-7}$M), fMLP ($10^{-7}$M), IL-8 ($0.75 \times 10^{-7}$M) or LTB4 ($10^{-7}$M). Migration was essentially complete within 2 hr. The last column of FIG. 7A reports migration of TNF-stimulated PMN through a collagen IV gel impregnated with fibrin.

Figure 8:
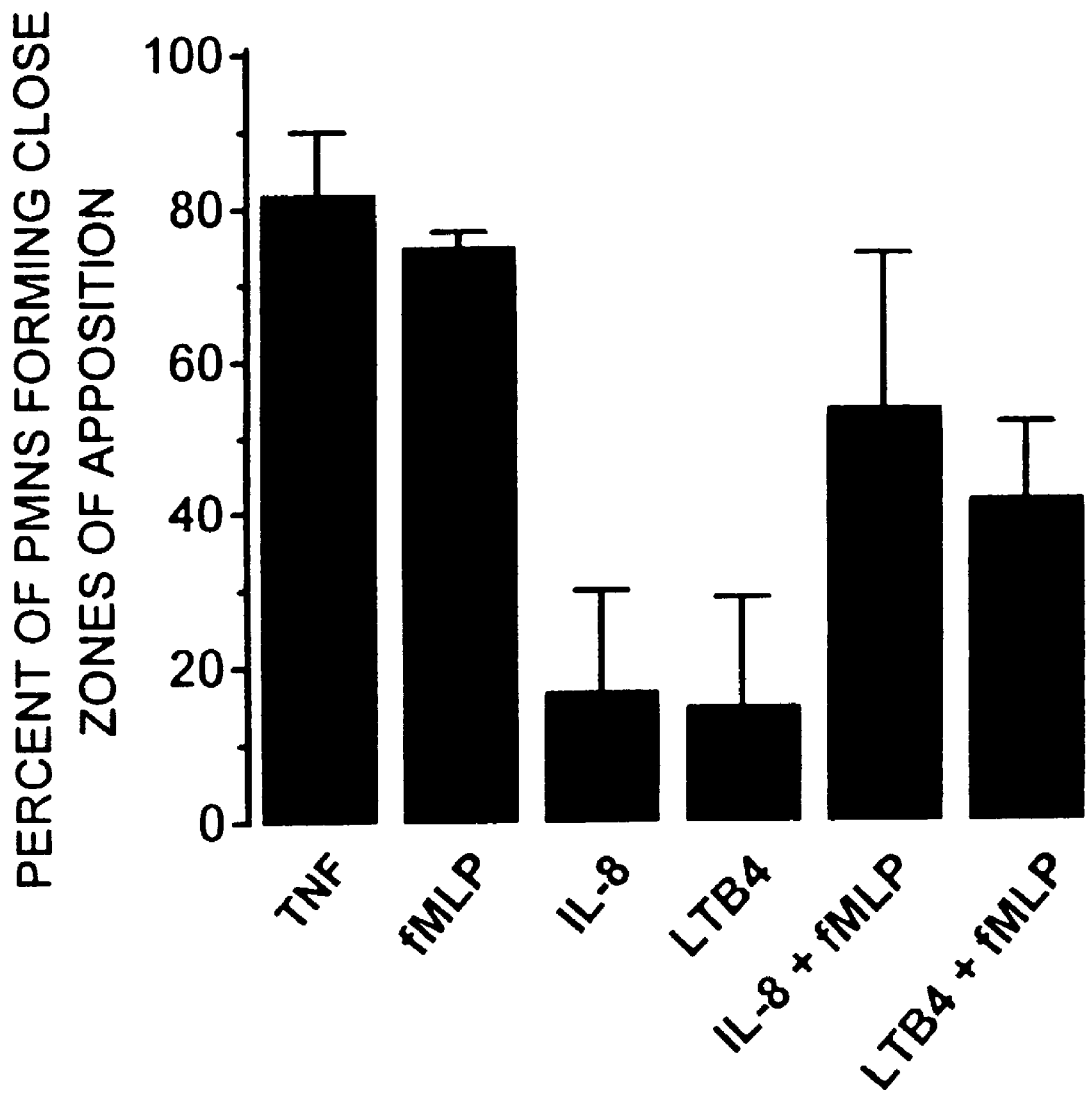

FIG. 8 shows "Closeness" of PMN apposition to fibrin matrices. PMNs stimulated with the indicated chemoattractants were allowed to adhere for 15 min to glass surfaces coated with fibrin as described under Experimental Procedures. PMNs forming close zones of adhesion are defined as those that exclude the entry of Rh-PEG into the area of adhesion between the cell and the underlying matrix as assayed by fluorescence microscopy. The concentrations of chemoattractants/cytokines used were the same as in FIG. 6. Less than 20% of unstimulated PMNs that adhered to the fibrin formed close zones of apposition.

Figure 9B:
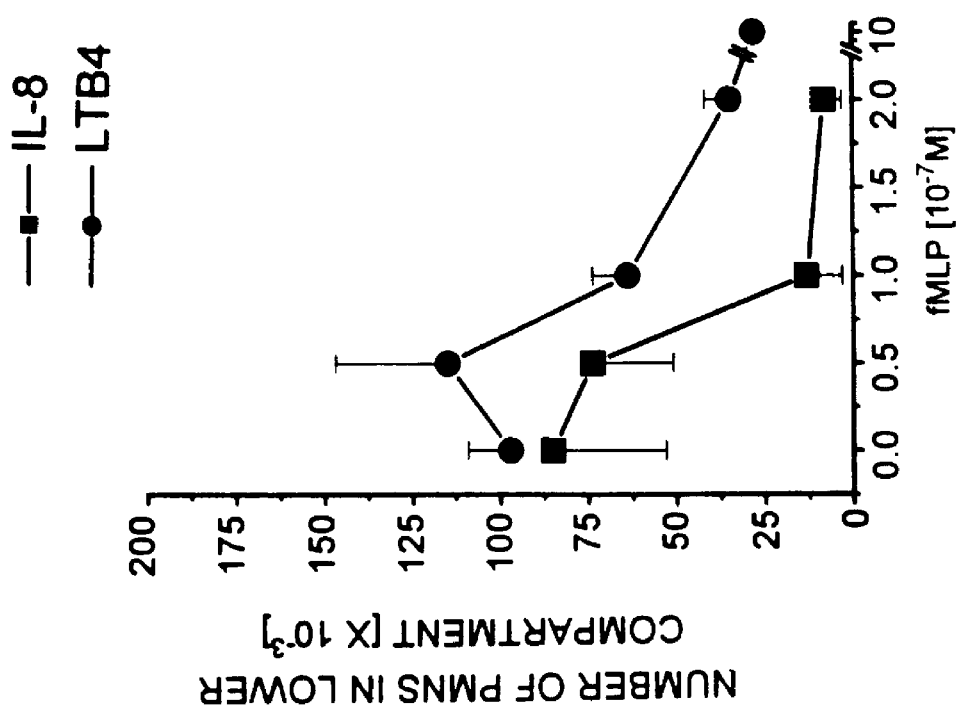
Figure 9A:
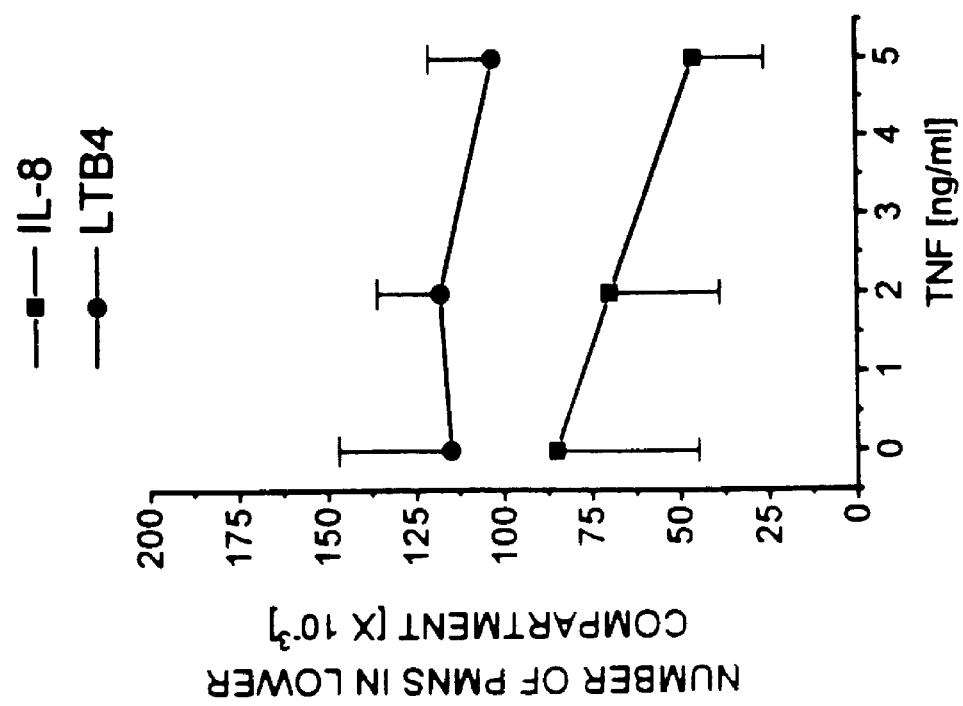

FIGS. 9A and 9B show the effect of combinations of chemoattractants/cytokines in promoting PMN migration through fibrin gels. PMN migration through fibrin gels was measured in response to TNF (A) or fMLP (B) added in combination to the bottom compartment, at the concentrations indicated. The concentrations of IL-8 and LTB4 used were the same as in FIGS. 5A, 5B, 5C, 5D, 5E, and 5F. PMN migration into the lower compartment was measured as described in FIGS. 1A and 1B after a 6 hr incubation at 37° C.

Figure 10A:
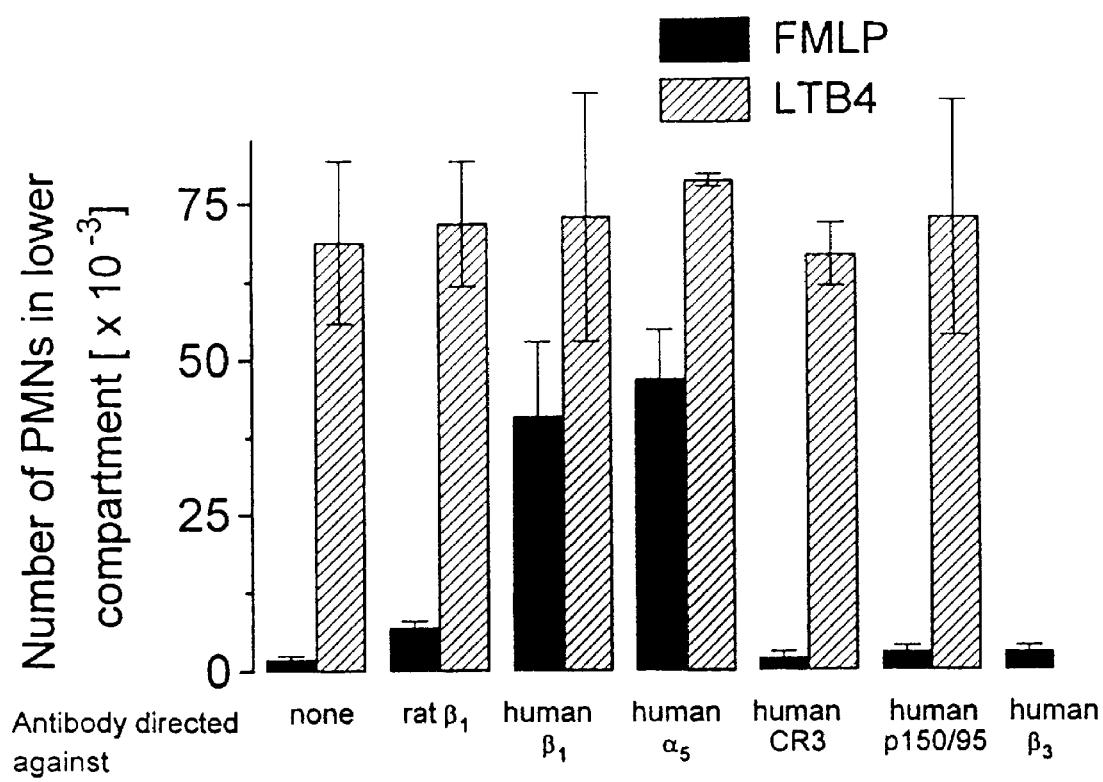

FIGS. 10A and 10B show that fMLP promotes PMN migration through fibrin gels when these cells are treated with antibodies directed against $\beta_1$ integrins (A) or incubated in medium containing synthetic peptide (B). Fibrin gels were formed on filters of cell culture inserts as described in Experimental Procedures and fMLP ($10^{-7}$M) or LTB4 ($10^{-7}$M) was added to the medium in the lower chamber. FIG. 10A—$10^6$ PMNs were pre-incubated in medium containing antibodies against rat or human $\beta_1$ integrins, or antibodies against the $\alpha5$ subunit of human $\alpha_5\beta_1$ integrin, or against the human $\beta_2$ integrin complement receptor 3 (CR3), or against the human $\beta_2$ integrin p150/95, or against human $\beta_3$ integrins for 15 min at 4° C. PMNs were placed in the upper chamber of cell culture inserts in the same medium and the inserts were incubated for 6 hrs at 37° C., at which time the number of cells in the lower chamber was determined using a Coulter Counter. FIG. 10B—$10^6$ PMNs were placed in medium containing the synthetic peptide GRGDSP (SEQUENCE ID NO. 1) (1 mg/ml) or the peptide GRGESP (SEQUENCE ID NO. 2) (1 mg/ml). The mixture was added to the upper chamber of cell culture inserts and the inserts were incubated for 6 hrs at 37° C., at which time the number of cells in the lower chamber was counted as in FIG. 10A.

Figure 11B:
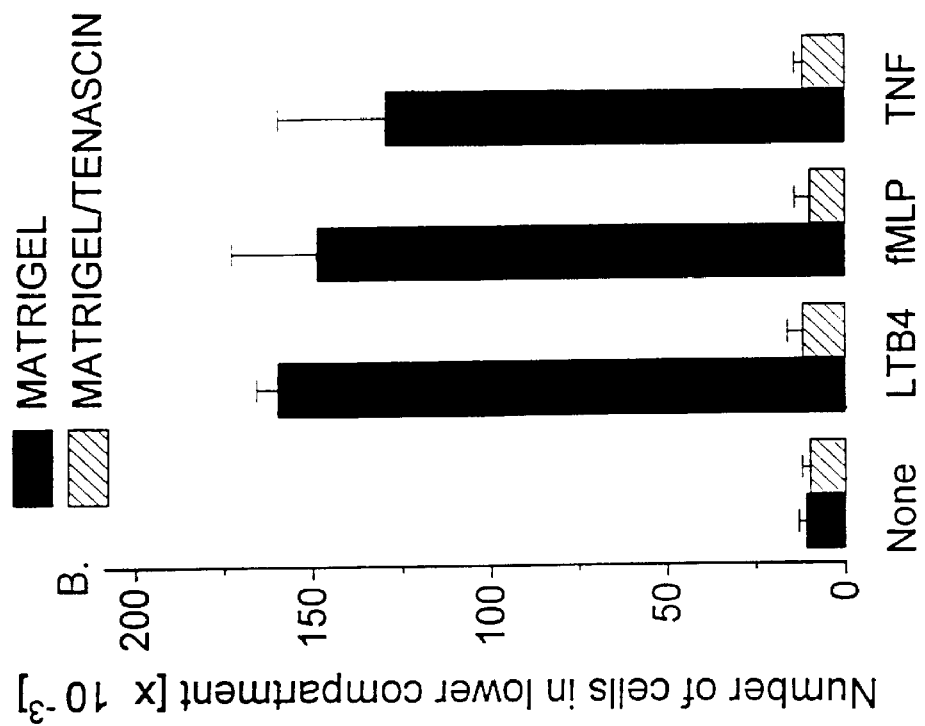
Figure 11A:
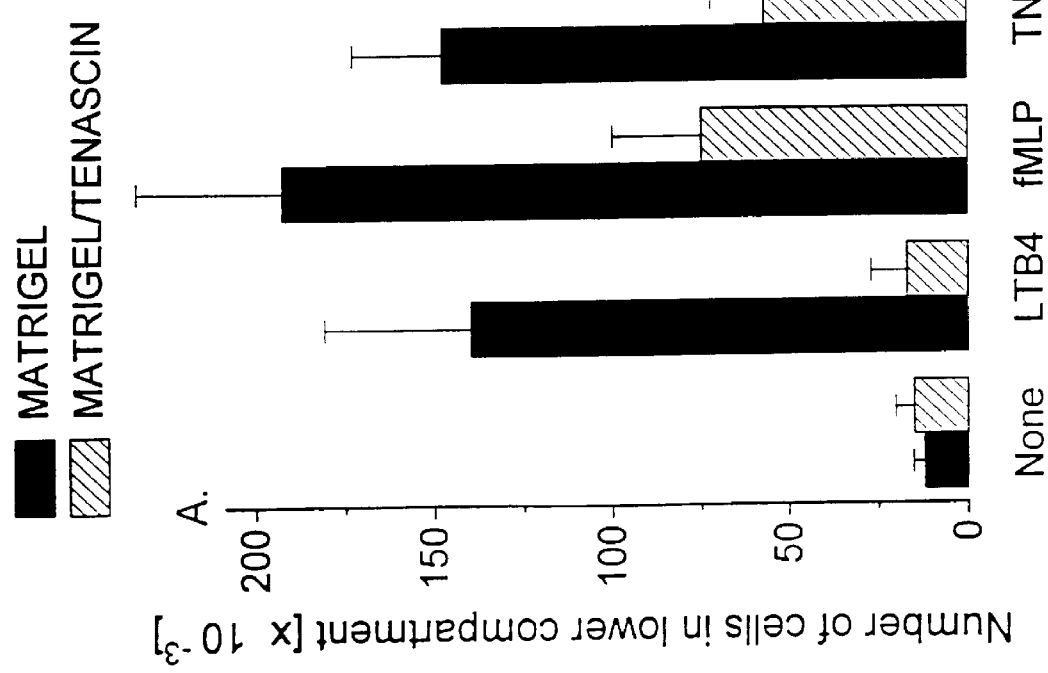

FIGS. 11A and 11B show that tenascin inhibits the chemotaxis of mononuclear phagocytes through Matrigel-coated filters. Cell inserts coated with either Matrigel or Matrigel and chick tenascin were prepared as described under Experimental Procedures. $10^6$ freshly harvested monocytes (A), or monocytes cultured for 24 h (B), were then added to the upper compartment and the indicated chemoattractant [TNF ($5 \times 10^{-7}$M), LTB4 ($10^{-7}$M) or fMLP ($10^{-7}$M)] was added to the lower compartment. The inserts were incubated for 24 h at 37° C. and the cells that migrated into the lower compartment were counted using a Coulter Counter.

FIG. 12 shows that chick tenascin inhibits the chemotaxis of PMNs through Matrigel-coated filters. Cell inserts coated with either Matrigel or Matrigel and chick tenascin were prepared as described under Experimental Procedures. $10^6$ freshly isolated PMNs were added to the upper compartment and the indicated chemoattractant [TNF ($5 \times 10^{-7}$M), LTB4 ($10^{-7}$M), or fMLP ($10^{-7}$M)], was added to the lower compartment. The inserts were incubated for 2–4 h at 37° C. and the cells that migrated into the lower compartment were counted using a Coulter Counter as in FIGS. 11A and 11B.

Figure 13A:
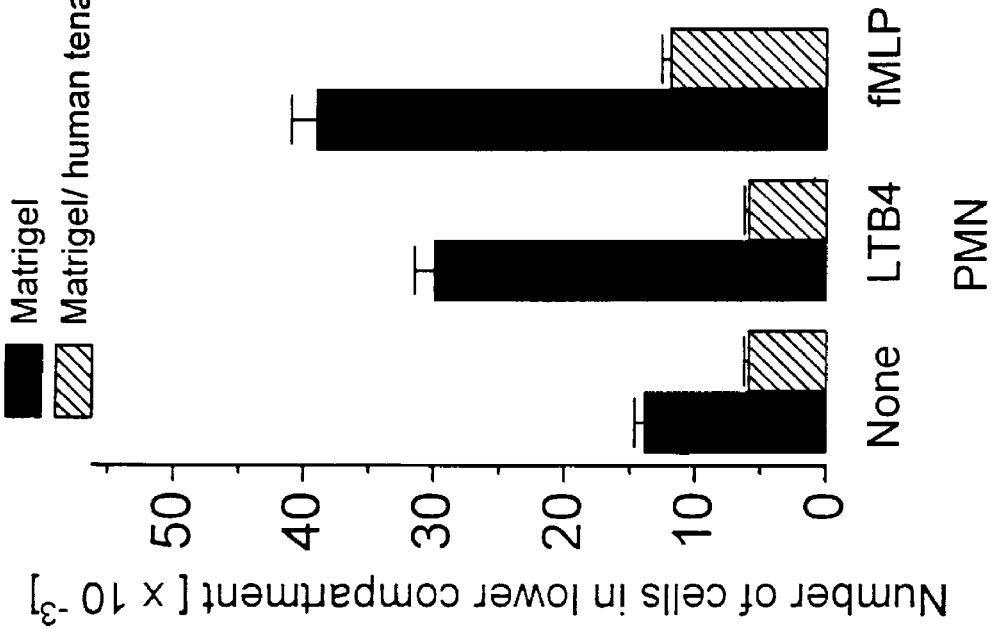
Figure 13B:
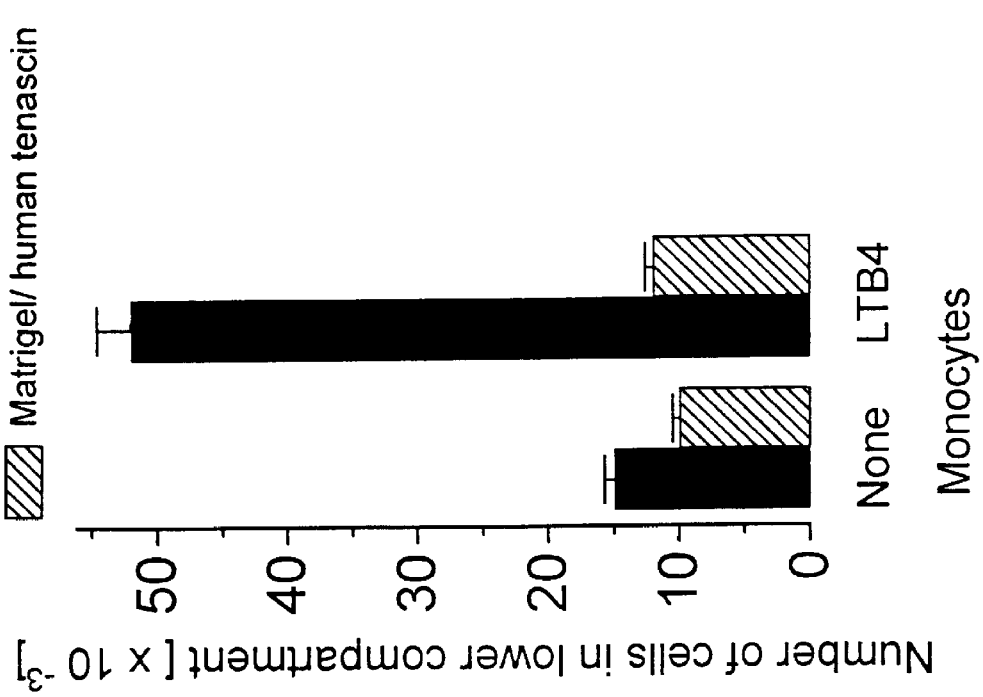

FIGS. 13A and 13B show that human tenascin inhibits the chemotaxis of monocytes or PMNs through Matrigel coated filters. Cell inserts coated with either Matrigel or Matrigel and human tenascin were prepared as described under Experimental procedures. $5 \times 10^5$ freshly isolated monocytes, or $10^6$ PMNs were added to the upper compartment and the indicated chemoattractant [fMLP ($10^{-7}$M) or LTB4 ($10^{-7}$M)] was added to the lower compartment. Migration of monocytes (A) was allowed to proceed for 24 h at 37° C. Migration of PMNs (B) was allowed to proceed for 6 h at 37° C. and the cells that migrated into the lower compartment were counted using a Coulter Counter as in FIGS. 11A and 11B.

Figure 14:
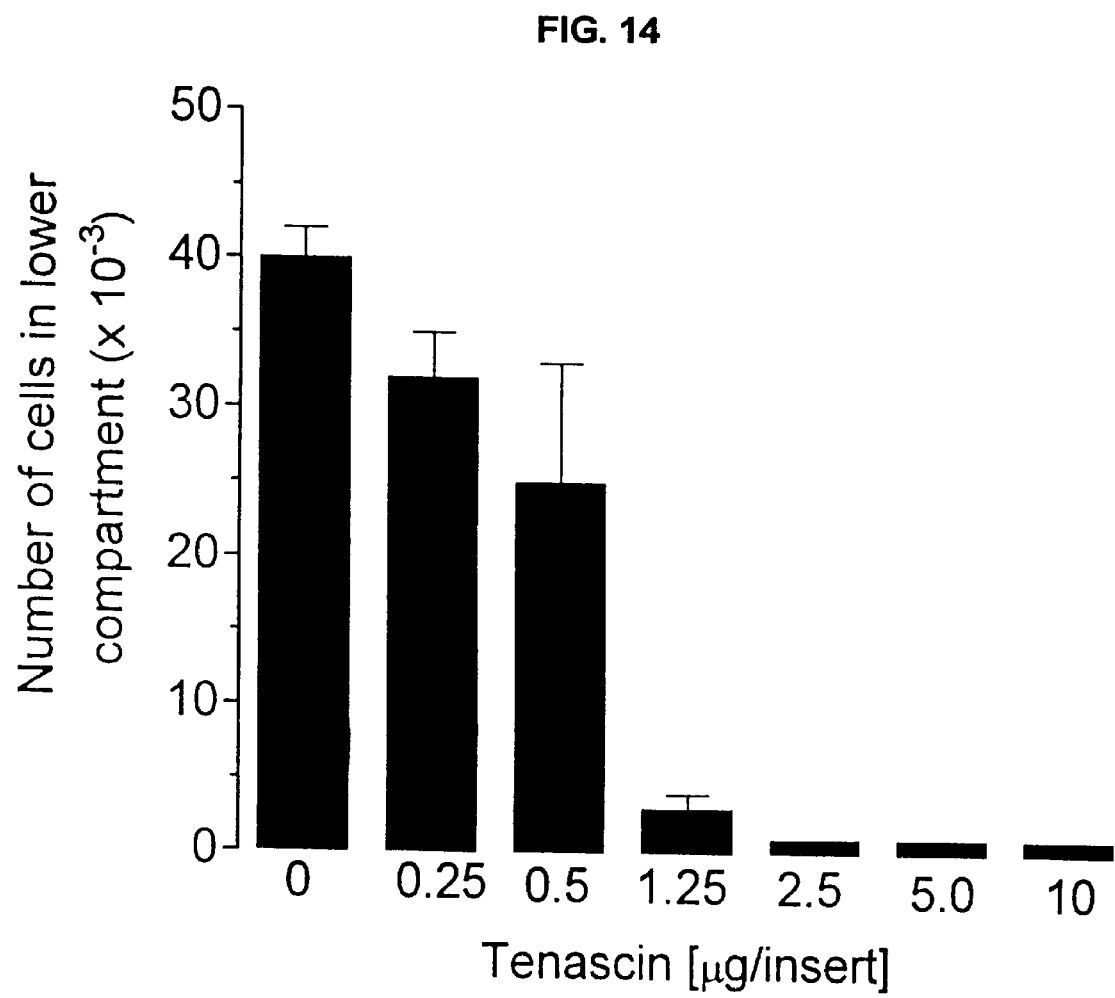

FIG. 14 shows that chick tenascin inhibits the migration of cultured monocytes through Matrigel-coated filters in a dose dependent fashion. Cell inserts were coated with Matrigel and then incubated with PBS containing the indicated concentrations of tenascin. The filters were washed with PBS. $2 \times 10^5$ cultured monocytes were added to the upper compartment. TNF ($5 \times 10^{-7}$M) was added to the lower compartment and the cells were allowed to migrate for 24 h at 37° C. This experiment is representative of 3 experiments.

Fewer than 1500 cultured monocytes migrated in the absence of any chemoattractant.

Figure 15:
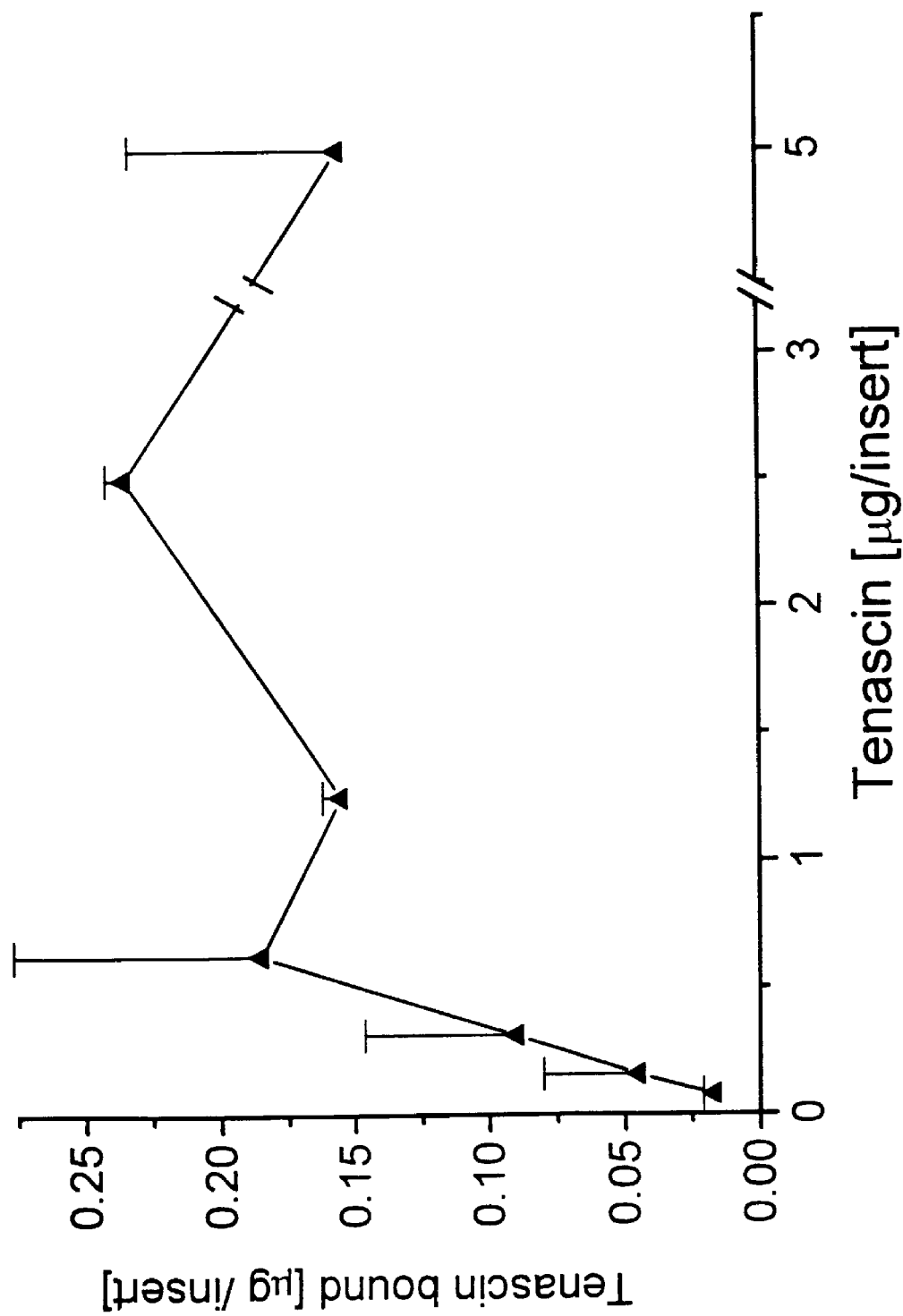

FIG. 15 shows binding of radiolabeled tenascin to Matrigel-coated filters. $^{125}$I-labeled chick tenascin was prepared as described under Experimental Procedures and mixed with unlabeled tenascin at a protein ratio of 1:100. This mixture was added to Matrigel-coated inserts in the amounts indicated and the inserts were incubated at 37° C. for 4 h, conditions identical to those used for the migration experiments described in FIGS. 11A and 11B. The filters then were washed, cut from the inserts, and counted in a LKB γ-counter.

FIG. 16 shows the effects of tenascin on the migration of cultured monocytes through filters coated with collagen I. Cell inserts were coated with 40 μg of collagen I. PBS containing 5 μg of chick tenascin was added to some of the inserts for 4 h as described under Experimental Procedures. $5 \times 10^5$ cultured monocytes were added to the upper compartment of the inserts and allowed to migrate for 24 h in the absence of a chemoattractant or in response to TNF ($5 \times 10^{-7}$M) or LTB4 ($10^{-7}$M) in the lower compartment. The cells that migrated into the lower compartment were counted as described in FIGS. 11A and 11B.

Figure 17B:
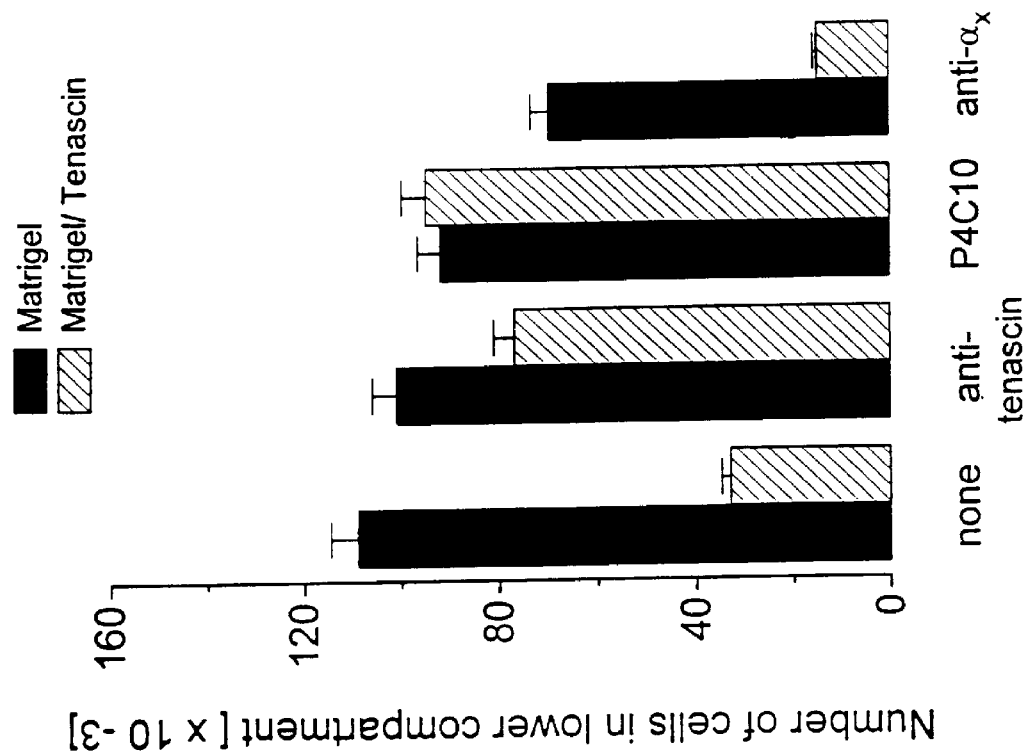
Figure 17A:
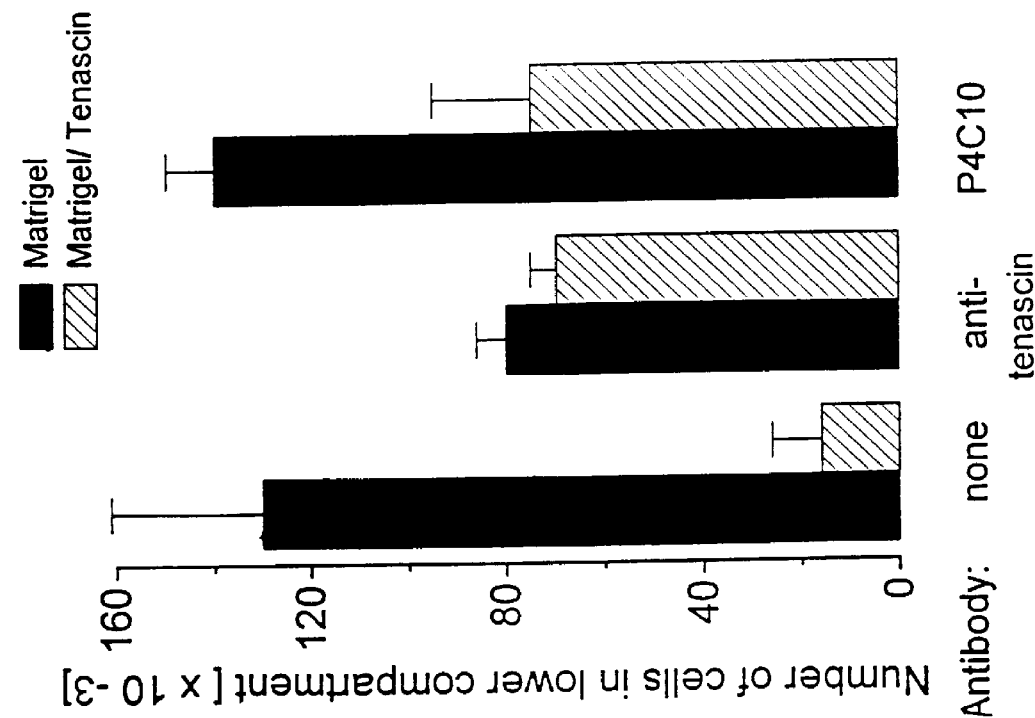

FIGS. 17A and 17B show that F(ab)'$_2$ fragments of anti-tenascin antibodies or anti-$\beta_1$ monoclonal antibodies promote monocyte and PMN chemotaxis through Matrigel/tenascin coated filters. $10^6$ freshly isolated monocytes (A) or PMNs (B) were used as described in FIGS. 11A, 11B and 12. Where indicated the cells were pre-incubated for 30 min at 4° C. with various antibodies [2 μg/ml] before adding them to the upper compartment of the chemotaxis chambers. The antibodies used were anti-tenascin (46), P4C10 (anti-$\beta_1$), and LeuM5 (7) (anti-$\alpha_x\beta_2$). The cells that migrated into the lower compartment at 24 h (A) and at 4 h (B) were determined as described in FIGS. 11A and 11B.

DETAILED DESCRIPTION OF THE INVENTION

The present invention provides a method of treating an infection caused by bacterial cells located on a surface of a foreign body over and around which fibrin has been deposited, the foreign body being present in a subject, which comprises administering to the subject an agent capable of inhibiting signalling mediated by a $\beta_1$ integrin cell surface receptor of leukocyte cells in an amount effective to enhance the migration of leukocyte cells into or through the fibrin so as to permit the leukocyte cells to reach and kill the bacterial cells and thereby treat the infection.

In one embodiment of the invention, the foreign body is a prosthetic device, a catheter, or a suture.

In another embodiment of the invention, the subject is a mammal such as a human.

In yet another embodiment of the invention, the leukocyte cells are polymorphonuclear leukocyte cells such as neutrophils, basophils, and eosinophils.

In another embodiment of the invention, the leukocyte cells are monocytes or macrophages.

In yet another embodiment of the invention, the agent is a peptide such as a peptide containing a $\beta_1$ integrin-binding domain. The agent can also be a peptidomimetic compound.

In another embodiment of the invention, the agent is an antibody or a fragment thereof that specifically binds to the $\beta_1$ integrin cell surface receptor of leukocyte cells.

The present invention also provides a method of preventing a chronic infection from occurring due to the presence of bacterial cells on a surface of a foreign body in a subject, which comprises coating the foreign body before placing it in the subject with a fibrinolytic agent capable of preventing the accumulation of fibrin on the surface of the foreign body so as to permit leukocyte cells to reach and kill any bacterial cells present on the surface of the foreign body and thereby prevent the chronic infection.

In one embodiment of the invention, the foreign body is a prosthetic device, a catheter, or a suture.

In another embodiment of the invention, the subject is a mammal such as a human.

In yet another embodiment of the invention, the fibrinolytic agent is plasminogen activator such as urokinase, streptokinase, or tissue plasminogen activator.

The present invention further provides a method of treating a malignant tumor comprising of malignant tumor cells over and around which tenascin has been deposited, the malignant tumor being present in a subject, which comprises administering to the subject an agent capable of inhibiting signalling mediated by a $\beta_1$ integrin cell surface receptor of leukocyte cells in an amount effective to enhance the migration of leukocyte cells through the tenascin so as to permit the leukocyte cells to reach and kill the malignant tumor cells and thereby treat the malignant tumor.

In one embodiment of the invention, the subject is a mammal such as human.

In another embodiment of the invention, the leukocyte cells are polymorphonuclear leukocyte cells such as neutrophils, basophils, and eosinophils.

In yet another embodiment of the invention, the leukocyte cells are monocytes or macrophages.

In another embodiment of the invention, the leukocyte cells are lymphocyte cells such as NK cells and killer cells.

In yet another embodiment of the invention, the agent is a peptide such as a peptide containing a $\beta_1$ integrin-binding domain. The agent can also be a peptidomimetic compound.

In another embodiment of the invention, the agent is an antibody or a fragment thereof that specifically binds to the $\beta_1$ integrin cell surface receptor of leukocyte cells.

The present invention also provides a method of treating a chronic inflammation in a subject caused by an increase in the number of leukocyte cells present at the site of the chronic inflammation which comprises administering to the subject an agent capable of stimulating signalling mediated by a $\beta_1$ integrin cell surface receptor of leukocyte cells in an amount effective to inhibit the migration of leukocyte cells toward the site of the chronic inflammation so as to reduce the number of leukocyte cells present at the site and thereby treat the chronic inflammation.

In one embodiment of the invention, the subject is a mammal such as human.

In another embodiment of the invention, the leukocyte cells are polymorphonuclear leukocyte cells such as neutrophils, basophils, and eosinophils.

In yet another embodiment of the invention, the leukocyte cells are monocytes or macrophages.

In yet another embodiment of the invention, the agent is a peptide such as a peptide containing a $\beta_1$ integrin-binding domain. The agent can also be a peptidomimetic compound.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

EXAMPLE 1

The evolution of many chemically distinct chemoattractants and receptors suggests that in addition to promoting adhesion and directing PMN locomotion these molecules might regulate the strength of PMN adhesion to specific matrix proteins. The findings that TNF stimulates PMNs to adhere to fibrinogen-coated surfaces via CD11c/CD18 (7,8), while phorbol dibutyrate stimulates PMNs to adhere to these surfaces via CD11b/CD18 (8,9), prompted the examination of the effects of different chemoattractants on PMN migration through three dimensional matrices composed of fibrin, collagen IV or Matrigel, and through gels formed by thrombin treatment of cell-free plasma.

EXPERIMENTAL PROCEDURES

Reagents

Human monocyte recombinant IL-8 (Ser-IL-8)$_{72}$ and TNF-α were from Upstate Biotechnology Incorporated (Lake Placid, N.Y.). LTB4, fMLP and Ficoll-Hypaque were from Sigma (St. Louis, Mo.). Rhodamine conjugated polyethylene glycol was prepared as described (10).

Preparation of Boyden-type chemotaxis chambers

Becton-Dickinson cell culture inserts (pore sizes 3 or 8 μm: Franklin Lakes, N.J.) were overlaid with the following proteins:

Fibrin gels: 1 Unit of thrombin (a gift from Dr. John Fenton, Albany Medical College, Albany, N.Y.), in 5 μl of PBS was added first to each insert. 0.1 ml phosphate buffered saline supplemented with $Ca^{2+}$ and $Mg^{2+}$ (PBS) containing 100 μg commercial grade fibrinogen (Calbiochem. Inc., San Diego, Calif.) or purified fibrinogen [a gift from Dr. Jeffery Weitz, (MacMaster University, Hamilton, On.)] was then placed into each 8.2 mm diameter insert on top of the thrombin. The mixture was incubated at 37° C. for 5 min to allow fibrin gel formation (determined by visual inspection). 1 Unit PPACK (Calbiochem Inc., San Diego, Calif.; $10^{-5}$M final concentration), in 100 μl medium was added to each insert to inhibit thrombin, and gels were washed with 250 μl PBS to remove inactivated thrombin. The fibrin gels formed were about 1 mm thick as measured under a dissecting microscope.

Collagen type IV and Matrigel matrices: 0.1 ml PBS containing 100 μg human placental collagen IV (Fluka Chemical Corp., Ronkonkoma, N.Y.), or 80 μg of reconstituted basement membrane proteins (Matrigel, Collaborative Research, Bedford, Mass.), was placed into each insert and allowed to gel at room temperature for 24 hrs.

Clotted Plasma: Whole blood was collected and the cellular components were removed by centrifugation. The resulting plasma was mixed with an equal volume of PBS, and 100 μl of this mixture was placed into each insert containing thrombin and allowed to clot as described above. One unit of PPACK in 100 μl PBS then was added and the inserts were washed with 250 μl of PBS.

Fibrinogen or fibronectin: 0.1 ml of PBS containing 100 μg/ml fibrinogen or fibronectin (New York Blood Center, New York, N.Y.), was placed into each insert (pore size 3 μm). Inserts were incubated at 37° C. for 60 min and washed with 250 μl of PBS. Filters coated with fibrinogen or fibronectin were diffusely fluorescent as visualized by epifluorescent microscopy when incubated with the corresponding antibody [fluorescein-labeled anti-fibrinogen, or anti-fibronectin monoclonal antibodies (Cappel, Malvern, Pa.)], while uncoated filters, or filters incubated with fluorescein-labeled antibody of the opposite specificity, were not.

PMN migration

PMNs were prepared from fresh heparinized blood from healthy adult volunteers by sedimentation on Ficoll-Hypaque gradients. Contaminating red blood cells were removed by hypotonic lysis, as described (7). The purity of PMN isolated by this method is >95% as determined by Wright-Giemsa staining (7). $10^6$ PMNs in 250 μl of PBS supplemented with 5.5 mM glucose and 0.1% human serum albumin (PBSG-HSA), were placed in the upper compartment of each insert and incubated for 0–6 hrs at 37° C. in a humidified atmosphere containing 95% air/5% $CO_2$. At the times and concentrations specified, chemoattractants/cytokines were added to the top or bottom compartment in 250 μl of PBSG-HSA. At the end of the incubation, the chambers were shaken to dislodge PMNs from the lower surface of the inserts. The medium in each lower compartment was collected and its content of PMNs was determined using either a Coulter Counter or a hemocytometer. Both methods gave similar results. Counts are expressed as the average number of PMNs that migrated into the lower compartment. Unless otherwise indicated, all values reported are the average of six data points from at least 3 independent experiments.

Confocal Microscopy

PMNs were suspended in medium containing 10 μM calcein/acetoxymethyl ester (Molecular Probes, Eugene, Oreg.), 0.02% (w/v) pluronic F-127 (Molecular Probes, Eugene, Oreg.), 2% heat inactivated calf serum (HyClone, Logan, Utah), and 0.2% DMSO, and mixed gently for 40 min at room temperature. Cells loaded with dye under these conditions exhibited no changes in motility (Mandeville and Maxfield, unpublished observations). The calcein-loaded cells were rinsed in PBSG-HSA and added to inserts containing fibrin gels in the presence or absence of TNF, fMLP, LTB4 or IL-8. Following incubation with PMNs, fibrin-coated filters were gently cut from their inserts using a razor blade, transferred to a glass slide, immersed in PBSG-HSA and covered with a glass coverslip. Migration of calcein-loaded PMNs through fibrin was analyzed using a Dialux 20 X microscope (Leitz) fitted with a K2 Bio confocal scanning optical attachment using a Nipkow spinning disk. The microscope was equipped with an image intensifier, charge coupled device camera and video frame averager. The surface of the fibrin gel was identified using reflection interference contrast microscopy. Cells were imaged with a Plan-neofluor 25 X fluorescence objective (NA=0.8) using fluorescein optics (490 nm excitation, 525 emission) and a spinning disk with pinhole apertures. Serial confocal optical sections were acquired at 1 μm intervals, digitized using the VolCon program (a PC-based image processing package, Indec Systems, Capitola, Calif.,). Three dimensional images were volume rendered using Microvoxel software (Index Systems), after passing data through a 3×3×3 Gaussian convolution filter. Each experiment was repeated at least twice using duplicate samples.

PMN adhesion to fibrin-coated surfaces

Fibrin coated Terasaki tissue culture plates were prepared as described (10). 5 μl of PBSG-HSA, containing PMNs ($10^6$/ml) and the indicated chemoattractant, was added to each well of the plate. Plates were incubated at 4° for 30 min to allow PMNs to settle to the bottom of the wells and warmed to 37° for 15 min to allow PMNs to adhere. Non-adherent cells were removed as described (7), and 2.5% glutaraldehyde in PBS added to fix the adherent PMNs. PMNs adherent to each well were enumerated using a phase-contrast microscope. Values reported are the mean number of PMNs adherent to six wells from a representative experiment (n=3).

Exclusion of rhodamine-labeled polyethylene glycol from zones of adhesion of PMNs to protein-coated surfaces 10 kDa rhodamine labeled polyethylene glycol (Rh-PEG), prepared and used as described previously (10), does not bind to untreated glass, tissue culture plastic, or to cell membranes. Rh-PEG binds avidly to protein-coated surfaces, and can be detected easily by its fluorescence. Individual wells on glass microslides (Carlson Scientific, Peotone, Ill.) were coated with either fibrin, Matrigel or collagen IV in a manner similar to that for coating cell culture inserts except that 20 μl of the various solutions were used per well. 20 μl of PMNs ($10^6$ cells/ml in PBSG-HSA) were added to each well and PMNs were allowed to adhere for 15 mins at 37°. The cells were washed in PBS, fixed with 3.7% paraformaldehyde in PBS for 10 min, washed again with PBS, and further incubated with 10 kDa Rh-PEG at room temperature for 60 min. The preparation then was washed with PBS and immediately observed by phase and fluorescent microscopy at 400× magnification. Average values from three different experiments are reported as the percentage of PMNs that excluded Rh-PEG from zones of adherence between the cells and the underlying matrix.

Degradation of $^{125}$I-labeled fibrin gels 1.0 ml PBS containing 1 mg human fibrinogen, 1 mCi of Na$^{125}$I (NEN, Boston, Mass.), and 1 Iodobead (Pierce, Rockford, Ill.) was incubated for 15 mins on ice. $^{125}$I-fibrinogen was separated from $^{125}$I by gel filtration over a Speedy Desalting Column (Pierce). >97% of the $^{125}$I recovered in the fibrinogen-containing fractions was precipitable with 20% trichloracetic acid. 5 μl PBS containing 1 Unit of thrombin, followed by 0.1 ml PBS containing $10^6$ cpm of $^{125}$I-fibrinogen (~10 μg) and 100 μg unlabeled fibrinogen were added to each insert, as described above. The resulting $^{125}$I-labeled fibrin gels were treated with PPACK, washed, and incubated with $10^6$ PMNs as described in the text. At various times after PMN addition the medium was removed from the upper and lower compartments, and added to 0.1 ml of PBS containing 10 mg/ml bovine serum albumin (BSA). Ice-cold trichloracetic acid was added to a final concentration of 20% and samples were centrifuged to sediment acid insoluble materials. TCA soluble and insoluble materials were separated by centrifugation and $^{125}$I in each fraction was determined using an LKB minigamma counter.

Results

IL-8 and LTB4, but not TNF or fMLP, promote the migration of PMNS through fibrin gels PMNs were placed into the upper compartment of inserts containing fibrin gels. IL-8, LTB4, fMLP, or TNF was placed in the medium in the lower compartment and the chambers were incubated at 37° C. for 6 hrs. IL-8 or LTB4 stimulated 12–25% of PMNs to migrate through the fibrin gels and into the lower compartment. In the absence of a chemoattractant or in response to various concentrations of TNF ($10^{-9}$–$5\times10^{-6}$M) or fMLP ($10^{-10}$–$10^{-6}$M), fewer than 0.3% of the PMNs migrated through fibrin gels into the lower compartments (FIGS. 1A and 2). Moreover, PMNs did not migrate through fibrin in response to the addition of 2–10% zymosan-activated human plasma (C5a) in the lower compartment.

PMNs stimulated by IL-8 or LTB4, but not by TNF or fMLP, migrated through fibrin gels formed by thrombin treatment of commercial-grade fibrinogen (FIG. 1A) or of purified fibrinogen, or through plasma gels formed by thrombin treatment of human plasma (FIG. 1B). Moreover, the presence of 20% human serum in the medium in both upper and lower compartments did not alter PMN migration through fibrin gels in response to IL-8, nor did the presence of serum promote PMN migration through fibrin gels in response to TNF or fMLP. That PMNs migrate through fibrin gels in the presence of human serum, and through gels formed from whole human plasma, indicates that IL-8 promotes PMN migration through fibrin gels containing the complex mixture of plasma proteins found under physiological conditions.

The percent of PMNs that migrated through fibrin gels varied with the concentration of IL-8 or LTB4 placed in the bottom compartment (FIG. 2B). Maximal PMN migration occurred with $0.7\times10^{-7}$M IL-8 or $0.2\times10^{-7}$M LTB4 (FIG. 2B). PMN migration decreased dramatically when IL-8 was used at concentrations >$10^{-7}$M, consistent with the report of Smith et. al. (11) that high concentrations of IL-8 desensitize PMNs. In contrast, there was no indication of PMN desensitization in response to supra-optimal concentrations of LTB4 (FIG. 2B).

To determine whether IL-8 and LTB4 promote PMN migration through fibrin gels by stimulating chemotaxis or chemokinesis we performed a checkerboard-type analysis (12). Few PMNs migrated through fibrin gels when IL-8 or LTB4 was placed in the upper compartment, or when the upper and lower compartments contained equal concentrations of IL-8 or LTB4 (FIGS. 1A and 1B). As the difference in IL-8 or LTB4 concentrations between the upper and lower compartments decreased, the number of PMNs that migrated through the fibrin gels also decreased (FIGS. 3A and 3B). These results indicate that PMN migration through fibrin gels in response to IL-8 or LTB4 reflects chemotaxis, not chemokinesis.

Between 25–50% more PMNs migrated through fibrin in response to LTB4 than to IL-8. It is unlikely that this difference reflects the response of different PMN subpopulations to LTB4 vs IL-8 since the same percentage of PMNs traversed fibrin gels in response to optimal concentrations of both LTB4 and IL-8 in the lower compartment as to LTB4 alone. Other investigators have reported that only 20–50% of PMNs migrate through filters (13), natural matrices, and cellular barriers (14), when stimulated by these chemoattractants. Since virtually all PMNs orient and crawl on surfaces when exposed to the chemoattractants (3), it is evident that all PMNs responded to them. The reason(s) why only a fraction of PMNs migrate through artificial or natural barriers in response to chemoattractants is unknown.

Figure 4:
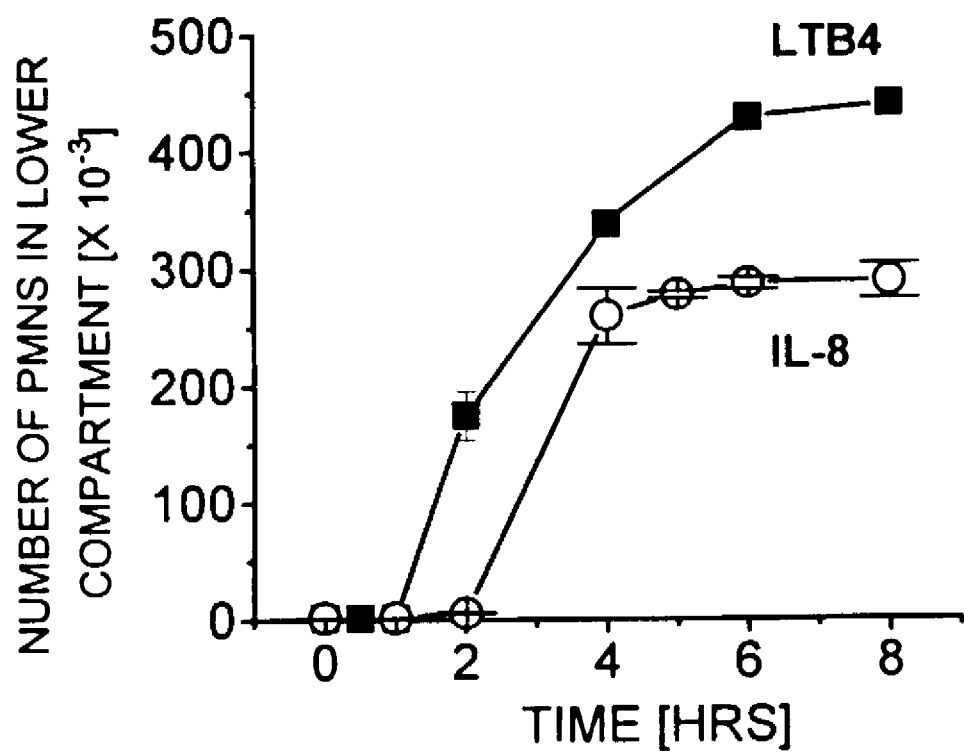
FIG. 4 shows a time course of PMN migration through fibrin gels. Fibrin gels were formed in cell culture inserts as described under Experimental Procedures. IL-8 ($0.75 \times 10^{-7}$M) or LTB4 ($10^{-7}$M) were added to the lower chamber. The number of PMNs that migrated through a fibrin gel was determined at the indicated times as described in FIG. 1A and 1B.
Figure 5E:
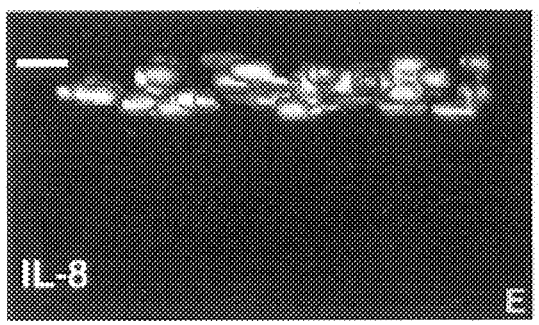
Figure 5F:
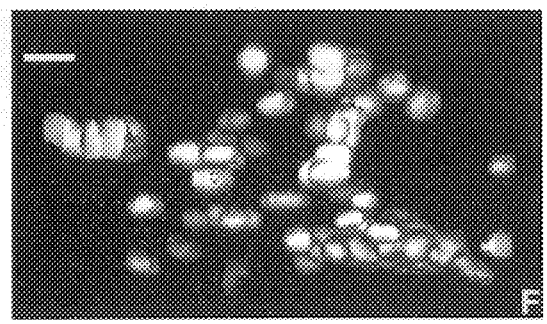

PMNs migrated through fibrin gels more rapidly in response to an optimal concentration of LTB4 than to an optimal concentration of IL-8 (FIG. 4). Ten percent of LTB4-stimulated PMNs migrated through fibrin gels within 2 hrs while fewer than 0.5% of IL-8-stimulated PMNs migrated through these gels in this time period (FIG. 4). By 6 hrs, maximal numbers of PMNs had migrated through fibrin gels in response to either IL-8 or LTB4.

To visualize the interactions of chemoattractant-stimulated PMNs with fibrin gels, PMNs prelabeled with calcein (15), were added to the upper compartment of inserts containing fibrin gels. Chemoattractants were added to the medium in the lower compartment, the chambers were incubated at 37° C., and at the times indicated the fibrin-coated filters were removed and examined by confocal microscopy. After a 1 or 4 hr incubation with fMLP or TNF, almost all the cells remained on the gel's surface; fewer than 5% of TNF- or fMLP-stimulated PMNs penetrated a short distance into the fibrin gels; (FIGS. 5A, 5B, 5C, 5D, 5E, and 5F). In contrast, greater than 80% of IL-8-stimulated PMNs migrated deeply into the fibrin gels after a 4 hr incubation (FIGS. 5A, 5B, 5C, 5D, 5E, and 5F). Greater than 80% of LTB4-stimulated PMNs began to migrate into the fibrin gel after 1 hr, while few IL-8 stimulated PMNs penetrated the fibrin at this time. These results show that TNF and fMLP do not promote PMN invasion of fibrin, and that LTB4 stimulates PMNs to enter fibrin gels more rapidly than IL-8. The latter finding is consistent with the more rapid transit of fibrin gels by LTB4- than IL-8-stimulated PMNs described in FIG. 4.

To further examine whether proteolysis of fibrin accounted for the selective ability of IL-8- or LTB4-stimulated PMNs to traverse these gels, the release of $^{125}$1I-labeled products was measured from 125I-fibrin incubated with PMNs for 6 hrs at 37° C. in the presence or absence of each of these chemoattractants. The rate and extent of release of $^{125}$I-labeled acid soluble and acid precipitable products was similar for all four chemoattractants (FIG. 6). Even in the presence of 20% serum, chemoattractant-stimulated PMNs released no more $^{125}$I-labeled products than unstimulated PMNs. These results suggest that fibrin degradation does not account for the selective ability of LTB4- and IL-8-stimulated PMNs to traverse fibrin gels.

LTB4, IL-8, TNF AND fMLP promote pmn migration through gels formed of matrigel and collagen IV To confirm that the inability of TNF-, fMLP-, or zymosan-activated human plasma-stimulated PMNs to migrate through fibrin gels reflected an effect of the interaction between the fibrin matrix and chemoattractant-stimulated PMNs, and not a general effect of any three dimensional matrix on PMNs stimulated with these chemoattractants, the ability of TNF, zymosan activated human plasma and fMLP to promote PMN migration through gels composed of basement membrane proteins (Matrigel) or collagen IV was examined (FIGS. 7A and 7B). TNF, fMLP, IL-8, zymosan-activated human plasma, or LTB4 added to the bottom chamber stimulated PMN migration through these gels (FIG. 7A). To determine whether fibrin affected PMN migration through collagen matrices, inserts coated with collagen IV gels were incubated with fibrinogen and thrombin to form fibrin sandwich on top of the collagen gels, and washed with PPACK-containing buffer. PMNs were added to the upper compartment and TNF to the lower compartment. The presence of fibrin prevented PMN migration through the collagen gels in response to TNF by about 75% (FIG. 7A). These results confirm that the effect of fibrin is selective and that it affects PMN migration in response to a specific subset of chemoattractants.

To determine whether protein monolayers had the same effects on PMN migration as gels, inserts were coated with fibrinogen or fibronectin. The adsorption of these proteins to the filters that form the floor of the inserts was confirmed by immunofluorescence microscopy, as described in Experimental Procedures. fMLP, TNF, IL-8 and LTB4 all promoted PMN migration through filters to which fibrinogen or fibronectin had been adsorbed (FIG. 7B).

PMNs adhere more closely to fibrin in response to fMLP or TNF than to LTB4 or IL-8

Is there a relationship between the ability of a chemoattractant to stimulate PMN migration through fibrin and its ability to promote close apposition of PMNs to fibrin? PMNs were incubated on fibrin-coated surfaces in the presence or absence of a chemoattractant for 15 min at 37° C. As expected, TNF, fMLP, LTB4 and IL-8 were equally effective in stimulating PMN adherence to fibrin (>200 chemoattractant-stimulated PMNs vs ~10 unstimulated PMNs adhered per mm$^2$). The closeness of PMN adhesion to fibrin was evaluated by the ability of 10 kDa Rh-PEG (8,10), to penetrate into the zones of adhesion between chemoattractant-stimulated PMNs and fibrin. By this measure 70–80% of adherent TNF- or fMLP-stimulated PMNs excluded Rh-PEG from their zones of contact with the fibrin (FIG. 8). In contrast, only about 15% of adherent LTB4- or IL-8-stimulated PMNs formed adhesive zones that excluded Rh-PEG (FIG. 8). Furthermore, the adhesive zones formed by this 15% of IL-8-stimulated PMNs were at least 50% smaller in area than those formed by TNF- or fMLP-stimulated PMNs as judged by the area from which Rh-PEG was excluded.

Previous studies (10) showed that the exclusion of fluorescein-conjugated F(ab)$_2$ anti-fibrinogen from zones of contact between ADP-stimulated platelets and fibrinogen-coated surfaces is a useful measure of the closeness of apposition between platelet membranes and the substrate. Therefore, the exclusion of fluorescein-conjugated F(ab)$_2$ anti-fibrin from zones of contact between LTB4- or IL-8-stimulated PMNs and fibrin was used as a measure of the interaction of these cells with fibrin-coated surfaces. About 50% of fibrin-adherent LTB4- or IL-8-stimulated PMNs formed adhesive zones that excluded this high molecular weight (100 kDa.) probe. As expected from studies with Rh-PEG (FIG. 8), >99% of fibrin-adherent TNF- or fMLP-stimulated PMNs excluded fluorescein-conjugated F(ab)$_2$ anti-fibrin from their zones of contact with fibrin (data not shown). Thus, LTB4- or IL-8-stimulated PMNs adhere more closely to fibrin than unstimulated PMNs, even though these chemoattractants do not promote the very close apposition characteristic of fMLP- or TNF-stimulated PMNs.

The effect of combinations of chemoattractants on migration of PMNS through fibrin gels The inability of fMLP- or TNF-stimulated PMNs to migrate through fibrin can be interpreted in at least two ways. First, fibrin blocks the capacity of PMNs to respond to fMLP or TNF. This seems unlikely since fMLP and TNF promote close apposition between PMNs and fibrin coated surfaces (FIG. 8). Second, fMLP or TNF signal PMNs to become sessile when they interact with fibrin. To examine the second possibility, the effects of combinations of chemoattractants on PMN migration through fibrin gels were monitored (FIGS. 9A and 9B). The presence of fMLP in the bottom compartment of the inserts reduced PMN migration through fibrin gels in response to IL-8 or LTB4 in a concentration dependent fashion. Higher concentrations of fMLP were required to effect equal inhibition of migration of LTB4-stimulated PMNs vs IL-8 stimulated PMNs (FIG. 9B). TNF had a small, reproducible, but statistically insignificant inhibitory effect on the migration of PMNs in response to IL-8 and no measurable effect on PMN migration in response to LTB4 (FIG. 9A). Thus, fMLP selectively reduced PMN migration through fibrin gels in response to IL-8 or LTB4 (FIG. 9B).

The effects of combinations of chemoattractants on formation of close apposition of adhesion of PMNs with fibrin were also examined. fMLP in combination with IL-8 or LTB4 induced about 50% of PMNs to form zones of adhesion that excluded 10 kDa. Rh-PEG (FIG. 8). In contrast, only 15% of PMNs stimulated with IL-8 or LTB4 alone formed close zones of adhesion (FIG. 8). Thus, the capacity of PMNs to form close zones of adhesion on fibrin was inversely associated with the capacity of PMNs to migrate through fibrin gels under conditions where PMNs were stimulated with TNF, fMLP, IL-8 or LTB4 given alone or with fMLP in combination with IL-8 or LTB4.

To determine the mechanism by which fibrin blocks PMN migration in response to fMLP, the effects of anti-integrin antibodies were tested (FIGS. 10A and 10B). PMNs incubated with anti-$\beta_1$ integrin antibodies (2 µg/ml) or the peptide GRGDSP (SEQUENCE ID NO. 1) (1 mg/ml), but not GRGESP (SEQUENCE ID NO. 2), migrated through fibrin gels in response to fMLP. Control experiments showed that anti-$\beta_1$ antibodies did not affect LTB4-stimulated PMN migration through fibrin. These studies show that interactions between PMN $\beta_1$ integrins and matrix-associated ligands regulate PMN migration. They suggest that fMLP, but not LTB4 signals binding of $\beta_1$ integrins to $\beta_1$ ligands (e.g. RDG) on fibrin. These studies also suggest that ligation of $\beta_1$ integrins signals fMLP-stimulated PMN to become sessile, and that by blocking $\beta_1$ integrins with antibodies or peptides, PMNs are able to migrate into tissue sites containing fibrin, from which PMN would otherwise be excluded.

Discussion

Matrix proteins modulate cellular responses to hormones, cytokines, and growth factors Matrix proteins exert profound effects on adhesion, differentiation, migration, and/or secretion of epithelial cells (16,17), endothelial cells (18), neurons (19,20) and leukocytes (7,9,21–27). Matrix proteins also affect the ability of many types of cells to respond to hormones, growth factors, and cytokines (28,29). The findings that some chemoattractants (e.g., fMLP, TNF, C5a), promote PMN migration in the context of two types of extracellular matrix proteins (e.g., matrigel and collagens IV) (FIGS. 5A, 5B, 5C, 5D, 5E, 5F, 7a, and 7B), and PMN immobilization in the context of another (e.g., fibrin) (FIGS. 1A, 1B, 2A, 5A, 5B, 5C, 5D, 5E, and 5F), are the first to show that specific matrix proteins regulate leukocyte chemotaxis. They show that fibrin gels, fibrin-impregnated collagen gels, and fibrin-containing plasma clots present selective barriers to the migration of fMLP- or TNF-stimulated PMNs and that chemotaxis of PMNs through three dimensional matrices is regulated by both the specific chemoattractant and the protein composition of the matrix with which the cells are in contact.

Matrix proteins regulate PMN adhesion, phagocytosis and secretion

Previous studies (7,9,21) have shown that TNF or phorbol ester stimulated PMNs adhere to fibrinogen-coated surfaces via different beta-2 integrins (CD11b/CD18 vs CD11c/CD18, respectively) and Lundgren-Akerlund et al. (22), and Thompson and Matsushima (23), have reported that fMLP stimulated PMNs adhere to protein coated surfaces with different efficiencies depending on the matrix protein used to coat these surfaces. With respect to phagocytosis, Pommier et al. (24), and Wright et al., (25) showed that the interaction of fibronectin with its $\beta_1$ integrin activates complement receptors (CD11b/CD18) on monocytes and PMNs to phagocytose C3bi-coated particles. With respect to secretion, Monboisse et al., (26,27) reported that the interaction of unstimulated or chemoattractant-stimulated PMNs with collagen I-coated surfaces induces the secretion of proteolytic enzymes and $O_2^-$. In contrast, preincubation of PMNs with collagen IV blocks the ability of collagen I and of fMLP to stimulate resting PMNs to secrete these products (26,27). Similarly, adhesion of TNF-stimulated PMNs to extracellular matrix proteins that express Arg-Gly-Asp motifs enhances PMN secretion (30). The findings reported here add chemotaxis to the list of leukocyte functions modulated by their contact with matrix proteins.

Relationship between strength of adhesion, closeness of PMN apposition to the substrate, and PMN migration DiMilla at al (31), have explored the relationship between strength of cell adhesion to a substrate and cell migration by following the spontaneous migration of human smooth muscle cells on surfaces that had absorbed varying concentrations of fibronectin or collagen IV. Under the conditions of their experiments, the rate of cell migration was maximal at an intermediate level of cell-substratum adhesiveness. Goodman et al. (32), found a similar biphasic relationship between the movement of murine skeletal myoblasts and the absorbed concentration of laminin on the substrate.

While the strength of PMN adhesion to fibrin was not measured directly, the "closeness" of apposition between PMNs' matrix-adherent surfaces and matrices containing different proteins was examined by measuring the permeability of zones of contact between PMNs and the underlying matrix to macromolecular probes. "Close" apposition is defined as the exclusion of 10 kDa Rh-PEG from zones of contact between the PMNs' substrate-adherent membranes and the matrix, and "loose" apposition as permeation of 10 kDa Rh-PEG into these zones. These results show that chemoattractants, such as IL-8 and LTB4, elicit "loose" apposition between PMNs and fibrin gels and promote PMN migration through these gels. Chemoattractants, such as FMLP and TNF, that signal "close" apposition between PMNs and fibrin gels do not promote PMN migration through these gels. This correlation was further supported by the findings that PMNs stimulated by any of these chemoattractants formed loose zones of adhesion (e.g., permeable to 10 kDa Rh-PEG) on collagen IV or Matrigel (FIG. 8), and migrated through these matrices (FIG. 7A); and that fMLP induced LTB4 or IL-8 stimulated PMNs to form close zones of apposition to fibrin and cease migration (FIGS. 8 and 9). Thus, there is an inverse association between close PMN interaction with a matrix protein and the ability of PMNs to migrate though gels containing it. These findings suggest that "close" and "loose" apposition between PMNs and matrix proteins as defined here, are functionally equivalent to very strong and intermediate adhesion between cells and matrix, respectively, as defined by DiMilla et al (31).

Fibrin degradation is not required for PMN chemotaxis

The zones of close apposition formed between fMLP- or TNF-stimulated PMNs and fibrin gels are impermeant to molecules of >10 kDa thereby excluding virtually all plasma protease inhibitors such as alpha$_1$ anti-plasmin and alpha$_2$ macroglobulin. Therefore, leukocyte proteases secreted into these zones function virtually uninhibited (33). In contrast, IL-8- or LTB4-stimulated PMNs adhere more loosely to fibrin-gels. Under these conditions, plasma protease inhibitors should have ready access to zones of contact with the substrate and inhibit the action of leukocyte proteases. Thus, fMLP- or TNF-stimulated PMNs might be expected to digest fibrin gels more efficiently than IL-8- or LTB4-stimulated PMNs. This was not observed (FIG. 6). There were no significant differences in the amount of radiolabel released from $^{125}$I-labeled fibrin by migrating LTB4- or IL-8-stimulated PMNs vs sessile fMLP- or TNF-stimulated PMNs, even in the presence of 20% serum. These findings suggest that PMNs that migrate through fibrin gels in response to IL-8 and LTB4 do so by mechanisms other than proteolyzing these gels. Lanir et al., (34) came to a similar conclusion in their studies of guinea pig macrophage migration through fibrin gels.

That fMLP and TNF promote PMN migration through fibrinogen-coated filters (FIGS. 7A and 7B), is probably related to the observations that fMLP-stimulated PMNs efficiently degrade substrate-adherent proteins including fibrinogen (33), and fibronectin (35), thereby removing these proteins from the substrate and facilitating PMN movement.

How do matrix proteins regulate leukocyte chemotaxis?

The results shown in Example 1 indicate the following: Different chemoattractants activate different subsets of PMN integrins to bind to ligands on matrix proteins (7–9). The interaction of each type of activated PMN integrin with its cognate ligand on a matrix protein specifies a distinct set of cellular migratory or sessile responses. These responses may result from direct interaction of a matrix protein with the activated integrin or by signals sent by the activated integrin to other integrins on the same cell. There are several instances where ligation of one type of integrin by matrix proteins modulates the activity of another type of integrin. As described above, Pommier et al., (24) and Wright et al. (25) showed that ligation of $\beta_1$ integrins by fibronectin activates the $\beta_2$ integrin CD11b/CD18, (complement receptor 3) on monocytes and PMNs to phagocytose C3bi-coated particles. It was previously shown that ligation of $\alpha 5\beta 1$ on platelets by fibronectin stimulates platelets to form close zones of apposition with fibrinogen (10). Hutalia et al, (36) reported that ligation of $\alpha_5\beta_1$ integrin by RGD peptides induces the expression of matrix metalloproteinases by fibroblasts, whereas ligation $\alpha_4\beta_1$ integrin by intact fibronectin suppresses matrix metalloproteinase expression.

In vivo inflammatory stimuli elicit the generation of multiple chemoattractants/cytokines. The present findings show that a hierarchy of cellular responses is generated when different combinations of chemoattractant receptors are stimulated simultaneously. Signals generated by fMLP receptors appear to override signals produced by LTB4 or IL-8 receptors, thereby blocking the ability of LTB4 or IL-8 to stimulate PMN migration through fibrin gels (FIG. 8). In contrast, signals generated by TNF receptors have no effect on LTB4-stimulated PMN migration through fibrin gels, and a very weak inhibitory effect on IL-8-stimulated PMN migration through these gels (FIG. 8).

PMN chemotaxis through three dimensional lattices composed of extracellular matrix proteins is regulated both by signals initiated by a specific chemoattractant, and by signals generated when specific PMN receptors interact with their cognate ligands on extracellular matrix proteins. Viewed from this perspective each of the many different chemoattractants provides PMNs both with general instructions to crawl, and with specific instructions to become sessile when specific receptors on these cells contact their cognate ligands on matrix proteins. Thus, chemoattractants provide tissue localization instructions for PMNs. It seems likely that chemoattractants also provide such instructions to other types of leukocytes as well.

PMNs stimulated with zymosan-activated human plasma (C5a) did not migrate across fibrin-coated inserts but did migrate across matrigel-coated inserts. Thus, C5a, like fMLP and TNF, signals PMNs to stop migrating when they contact fibrin.

EXAMPLE 2

The inhibitory effects of extracellular matrix proteins on chemotaxis of leukocytes (7,8,9,65) prompted the examination the effects of tenascin on these processes. The present findings show that tenascin blocks chemotaxis of polymorphonuclear and mononuclear phagocytes across reconstituted basement membrane (Matrigel)-coated filters in a $\beta_1$ integrin-dependent process.

EXPERIMENTAL PROCEDURES

Cells

Polymorphonuclear leukocytes (PMN), were prepared as described (7) from heparinized human blood by sedimentation on Ficoll-Hypaque gradients. Contaminating red blood cells were removed by hypotonic lysis. The purity of PMN isolated by this method was >95% as determined by Wright-Giemsa staining.

Mononuclear cells were isolated by centrifugation of heparinized human blood on Ficoll-Hypaque gradients as described (65,66). The mononuclear cell fraction was resuspended in RMPI 1640 medium supplemented with 10% pooled human serum or autologous serum and used immediately for monocyte migration studies. For some experiments, monocytes were obtained by centrifugation of whole blood or of white blood cells concentrated from a unit of blood (leukopak), on Nycodenz gradients as described (39). More than 90% of the nucleated cells obtained by this Nycodenz method were monocytes, as assessed by their ability to phagocytose IgG-coated red blood cells.

Cultured monocytes were prepared by allowing $10^7$ total mononuclear cells, suspended in 10 ml of RMPI 1640 medium supplemented with 10% pooled human serum (1640+HS), or 10% autologous serum (1640+AS), to adhere to Falcon T-150 tissue culture Petri dishes for 2 h at 37° C. Non-adherent cells were removed by washing, leaving an adherent cell population consisting of greater than 98% monocytes as measured by their capacity to phagocytose IgG coated sheep red blood cells. For migration studies, monocytes were maintained in culture for 24 h in RPMI 1640+HS or AS, and detached from the dishes by gentle pipetting of 10 ml of ice cold phosphate buffered saline (without $Ca^{2+}$ or $Mg^{2+}$) containing 1.0 mM EDTA. The cells recovered were resuspended in RPMI-1640+HS as described (65).

Protein-coated filters

Cell culture inserts containing polyethylene terephthalate filters, 8-$\mu$m pore size (Becton-Dickinson), were overlaid with 0.1 ml of Matrigel (20–25 $\mu$g protein/filter) (Collaborative Research, Bedford, Mass.), and incubated at room temperature until they dried. These Matrigel-coated filters were washed with phosphate buffered saline containing 1.0 mM $Mg^{2+}$ and 1.0 mM $Ca^{2+}$ (PBS). 0.1 ml of a PBS solution (pH 7.2) containing the indicated amount of purified chick brain tenascin was added to some of the inserts. The filters were incubated at room temperature until they dried. These protein-coated filters were washed again with PBS and used within 12 h for cell migration studies. To prepare collagen I-coated inserts, filters were coated with rat tail collagen I (ICN Biochemicals, Costa, Mesa, Calif.) (400 $\mu$g/ml in PBS), by adding 0.1 ml of this solution to an insert and incubating the inserts at room temperature for 24 h. Some of these collagen I-coated filters were then incubated with tenascin as described above.

Cell migration

Monocytes: Cell culture inserts were placed in 16 mm wells containing 0.5 mls of RPMI-1640+HS or AS in the presence or absence of a chemoattractant. 0.5 ml of RPMI-1640+HS or AS serum containing between 2–10×$10^5$ mononuclear phagocytes was added to the upper chamber of the inserts and the inserts were placed in a humidified $CO_2$ incubator at 37° C. After 24 h the medium in the lower chamber was recovered and its cell content assayed using either a Coulter counter or a hemocytometer. No significant increase was observed in the number of monocytes that migrated into the lower compartment at times greater than 24 h. Cell counts reported are the average number of cells recovered from the medium in the lower compartment of chemotaxis chambers. Over 90% of the cells in the lower chamber were identified as monocytes based on their morphology, their capacity to phagocytose IgG coated sheep red cells, and their staining with fluorescein-conjugated anti $\alpha_m\beta_2$ monoclonal antibody (Oncogene Sciences, Uniondale, N.Y.). Unless otherwise indicated, all values are the average of duplicate samples run in parallel in a representative experiment. Each experiment was repeated at least three times with similar results.

PMN: 250 μl of PBS [supplemented with 5.5 mM glucose and 0.1% human serum albumin (HSA) (PBSG-HSA)] containing 1×10⁶ PMNs was placed in the upper compartment of each insert. 250 μl of PBSG-HSA with or without chemoattractant, as indicated, was added to the bottom compartment. The inserts were incubated for about 4 h at 37° C. in a humidified atmosphere containing 95% air/5% $CO_2$. No further increase in the number of PMNs was observed in the lower compartment beyond 4 h. The medium in the lower compartment was collected and its content of PMN determined using a Coulter Counter, as described in Example 1.

Tenascin

To isolate tenascin, 14-day embryonic chick brains were homogenized in the presence of protease inhibitors and the extracts were clarified as previously described (61). Dry CsCl was added to a final concentration of 0.5 g/ml and the extract was centrifuged (18 h, 45,000 rpm, 20° C.) in a Beckman VAC 50 rotor. The resulting density gradients were fractionated into five 8-ml fractions. The third and fourth fractions a rich source of relatively pure tenascin, were pooled, dialyzed versus 10 mM Tris pH 8.0, then incubated with chondroitin ABC lyase (Seikagaka America), in the presence of protease inhibitors (61), to degrade contaminating proteoglycans. The sample then was lyophilized, resuspended in 4M guanidine-HCl/0.1M Tris (pH 7.6), and fractionated on a 1.5×100 cm column containing Sephacryl S-500 (Pharmacia, Piscataway, N.J.), equilibrated in the same buffer. Tenascin-rich fractions were pooled, dialyzed, lyophilized, resuspended in a small volume of guanidine buffer, and finally dialyzed extensively vs PBS. This procedure yielded large amounts of purified tenascin which migrated as characteristic 220, 200, and 190 kD polypeptides when analyzed by SDS-PAGE under reducing conditions (44). Human tenascin was obtained from GIBCO-BRL, (Grand Island, N.Y.). To remove the detergent in the preparation, the sample was run over a gel filtration column in the presence of 4M guanidine-HCl; the tenascin containing fractions were then dialyzed extensively vs PBS.

Measurement of tenascin bound to matrices

Chick tenascin was radiolabeled using chloramine T (67), and mixed with unlabeled tenascin at a 1:100 protein ratio. 250 μl of PBS containing varying amounts of this mixture was added to inserts coated with Matrigel or collagen I. The inserts were incubated at room temperature for 4 h at 37° C. in a humidified 95% air/5% $CO_2$ atmosphere and washed with PBS. The filters were cut from the inserts with a scalpel, and assayed for $^{125}I$ in a Beckman gamma counter.

Reagents

Monoclonal antibody P4C10 (anti-β chain of human beta-1 integrin), was from GIBCO-BRL. Fluorescein conjugated monoclonal antibody against the β chain of human beta-2 integrins (anti-$β_2$-CP14F) was obtained from Oncogene Sciences (Uniondale, N.Y.). Fluorescein conjugated anti CD11b monoclonal antibody was from AMAC Inc. (Westbrook, Me.). Monoclonal anti-CD11c/CD18 (LeuM5) was from Organon-Toknika Inc.(Malvern, Pa.). F(ab)'₂ fragments of anti-tenascin antibodies were prepared as described (46). Chondroitin sulfate proteoglycan monomers were purified and antibodies prepared against these proteoglycan monomers as described (37). The F(ab)'₂ fragments used in the present study were prepared from total anti-proteoglycan IgG. These antibodies were not further purified by affinity chromatography and therefore recognize both 400 kD and 250 kD proteoglycan core proteins (67).

Results

Tenascin blocks chemotaxis of monocytes and neutrophils, through matrigel-coated filters About 20% of freshly isolated human monocytes, 15% of cultured monocytes and 10% of PMNs migrated through Matrigel-coated culture inserts in response to fMLP, LTB4, or TNF (FIGS. 11A, 11B, and 12). Monocytes began to appear in the lower compartment at 12 h, and reached maximum numbers by 16–24 h. PMNs began to appear in the lower compartment by 2 h, and reached a maximum by 4 h. Fewer than 2% of added monocytes or PMN, migrated into the lower compartment in the absence of a chemoattractant (FIGS. 11A, 11B, and 12).

Addition of chick brain tenascin to the Matrigel significantly reduced monocyte and PMN migration in response to TNF, fMLP or LTB4 (FIGS. 11A, 11B and 12). The presence of tenascin had no significant effect on the limited number of monocytes that migrated in the absence of chemoattractant (FIGS. 11A and 11B). In contrast, tenascin further reduced the small number of PMN that migrated across Matrigel in the absence of chemoattractant (FIG. 12). The extent to which tenascin inhibited chemoattractant-stimulated monocyte or PMN migration varied from 65–80% depending on the chemoattractant used (FIGS. 11A, 11B, and 12). The ability of tenascin obtained from cultured human glioma cells to effectively inhibit leukocyte migration was examined. Indeed, the addition of 5 μg of human tenascin to the Matrigel-coated filters reduced the number of monocytes or PMNs migrating in response to a chemoattractant by at least 50% (FIGS. 13A and 13B).

The effect of chick brain tenascin on TNF-stimulated migration of monocytes varied with the amount of tenascin added (FIG. 14). Addition of about 0.75 μg tenascin caused half maximal inhibition of TNF-stimulated monocyte migration (FIG. 14). To confirm that tenascin bound to the Matrigel, Matrigel-coated inserts were incubated with varying amounts of concentrations of $^{125}I$-labeled chick tenascin for 4 h at 37° C. The inserts then were washed with PBS and the bound radioactivity was determined. Near plateau binding of radiolabeled tenascin was obtained with the addition of 0.625–1.25 μg of chick tenascin to the Matrigel coated filters (FIG. 15). This resulted in the adsorption of about 0.2 μg of tenascin per filter. Once bound, less than 1% of the $^{125}I$-labeled tenascin eluted from the filters into either the upper or lower compartment of the chambers during a 4–6 h incubation at 37° C. Thus, ~99% of tenascin remained bound to Matrigel-coated filter. The capacity of tenascin to inhibit monocyte migration (FIG. 14) was roughly proportional to the amount of tenascin that bound to the filter (FIG. 15), indicating that tenascin bound to the Matrigel matrix, not soluble tenascin, blocked monocyte and PMN migration.

Tenascin blocks migration of monocytes through collagen I gels

The effects of tenascin on monocyte migration through another extracellular matrix, collagen I were examined. Twelve percent of TNF- and 18% of LTB4-stimulated monocytes migrated through cell culture inserts coated with collagen I (FIG. 16). Addition of chick brain tenascin to collagen I coated inserts reduced TNF- or LTB4-stimulated monocyte migration by at least 60% (FIG. 16). Binding studies with $^{125}I$-labeled chick tenascin revealed that similar amounts of tenascin bound to collagen I-coated filters as to Matrigel-coated filters.

Effect of F(ab)'₂ anti-tenascin on the migration of monocytes across filters coated with matrigel and tenascin Monocytes or PMN were added to the upper compartment of inserts coated with Matrigel alone or with Matrigel and tenascin. F(ab)'$_2$ anti-tenascin (2 μg/ml) was added to the medium in the upper compartment and LTB4 ($10^{-7}$M) was added to the lower compartment. F(ab)'$_2$ fragments of anti-tenascin antibody had no significant effect on PMN migration across filters coated with Matrigel alone (FIG. 17A), but reduced monocyte migration across this matrix by about 40% (FIG. 17B). However, F(ab)'$_2$ fragments of anti-tenascin antibody restored PMN chemotaxis across filters coated with Matrigel and tenascin to about 75% of control values (FIG. 17B), and increased substantially monocyte migration across tenascin coated Matrigel (FIG. 17A).

Because of their affinity for tenascin, proteoglycans may contaminate some tenascin preparations (46). Therefore, the effects of F(ab)'$_2$ fragments of polyclonal anti-proteoglycan on monocyte migration across filters coated with tenascin and Matrigel were examined. F(ab)'$_2$ anti-proteoglycan (2–5 μg/ml) did not reverse tenascin's inhibitory effect on monocyte migration across filters coated with Matrigel and tenascin, and did not significantly affect monocyte chemotaxis across filters coated with Matrigel alone. These studies suggest that tenascin inhibits migration by interacting with monocytes and not by blocking some matrix component required for their migration.

Antibodies that block $\beta_1$ integrins reverse the inhibitory effects of tenascin on monocyte and pmn migration through filters coated with matrigel and tenascin Endothelial cell attachment and spreading on human tenascin has been shown to be partially mediated by $\beta_1$ integrins (60). Similarly, Prieto et al. (53,54), showed that anti-$\beta_1$ integrin antibodies block the adhesion of glioma and carcinoma cell lines to tenascin. Therefore, the effects of anti $\beta_1$ antibodies on monocyte and PMN chemotaxis through filters coated with Matrigel alone or with Matrigel and tenascin were examined. Monocytes or PMNs were preincubated for 30 min at 4° C. in medium containing 2 μg/ml of the test antibody. The suspension then was added to the upper compartment of the inserts.

LTB4 was added to the lower compartment and the inserts were incubated at 37° C. for 24 h for monocytes or 4 h for PMN. A monoclonal antibody directed against $\beta_1$ integrins (P4C10) had no effect on monocyte chemotaxis through filters coated with Matrigel alone but reversed the inhibitory effect of tenascin on monocyte migration through Matrigel/tenascin coated filters by about 50% (FIGS. 17A and 17B). Control experiments showed that monoclonal antibody P4C10 also reversed tenascin's inhibitory effect on TNF-stimulated monocyte chemotaxis by about 60%. P4C10 reversed almost completely the inhibitory effect of tenascin on LTB4- (FIG. 17B) or TNF-stimulated chemotaxis of PMN across filters coated with Matrigel and tenascin.

To confirm that the effect of P4C10 was due to its interaction with $\beta_1$ integrins, the effects of other anti-integrin antibody, $A_{II}B_{II}$, on chemotaxis of monocytes through filters coated with Matrigel and tenascin were examined. $A_{II}B_{II}$ (2 μg/ml) blocked the inhibitory effect of tenascin on monocyte chemotaxis, allowing LTB4 stimulated monocytes to migrate through Matrigel/tenascin coated filters. In contrast, an antibody (LeuM5) directed against $\alpha_x$ (p150/95), a member of the $\beta_2$ integrin family found on both PMNs and monocytes, did not reverse tenascin's inhibitory effect on LTB4-stimulated chemotaxis of PMN or monocytes through Matrigel/tenascin-coated filters (FIGS. 17A and 17B). As expected, monoclonal antibody IB4, directed against leukocyte $\beta_2$ integrins, inhibited chemotaxis of monocytes and PMNs across filters coated with Matrigel alone or with both Matrigel and tenascin. Thus, antibodies directed against members of the $\beta_2$ integrin family did not reverse tenascin's inhibitory effect on monocyte and PMN chemotaxis. These results indicate that blocking the interaction of monocytes or PMNs with tenascin, either by masking the tenascin on the matrix with F(ab)'$_2$ anti-tenascin or by blocking $\beta_1$ integrins on the cells, reversed the inhibitory effect of tenascin on monocyte and PMN chemotaxis.

Discussion

PMNs migrate through matrices formed by, and containing, proteins that are "normal" constituents of basement membranes and of the ground substance of interstitial spaces (e.g., collagens I and IV, laminin), in response to all chemoattractants tested (fMLP, TNF, C5a, IL-8, LTB4) (68,69). In contrast, whether PMN migrate through matrices composed of, or containing, fibrin depends upon the specific chemoattractant with which they have been stimulated. For example, fMLP, TNF and C5a stimulate PMNs to adhere tightly to fibrin gels, but not to migrate into or through them. In contrast, IL-8 and LTB4 stimulate PMNs to migrate efficiently through these gels.

The capacity of specific chemoattractants to signal cessation of migration when PMNs contact fibrin suggested that this might be a mechanism by which these cells are excluded from some tissue compartments, and concentrated in others. One example, however, hardly establishes a general principle. Therefore, other matrix proteins that block PMN and monocyte chemotaxis were sought.

Tenascin inhibits PMN and monocyte chemotaxis through collagen I or Matrigel Matrices Addition of tenascin to three-dimensional matrices formed by collagen I or Matrigel signals cessation of movement of PMNs and monocytes in response to all three chemoattractants tested (fMLP, LTB4, TNF) (FIGS. 11–17). The capacity of tenascin to block chemotaxis of PMNs stimulated by LTB4 is of special note since LTB4 promotes PMN migration through fibrin gels (25). This finding supports our contention that leukocyte migration through extracellular matrix is regulated by both the proteins in the matrix and the specific chemoattractant. It demonstrates that a chemoattractant can have entirely different effects on a single class of leukocyte, depending upon the matrix proteins with which the leukocyte is in contact.

One of tenascin's functions in adults is to inhibit PMN and monocyte entry into specific tissue compartments Tenascin is an unusual matrix protein. It is expressed widely in embryonic tissues where it regulates cell migration during organogenesis. Under physiological conditions in adults, tenascin is absent from most tissues, except lymphoid tissue (40,55), and brain (43). However, under pathological conditions, tenascin synthesis is stimulated. It is deposited in the extracellular matrix in areas of vascular injury (57), and tumor stroma (43,63), which are also areas of fibrin deposition (59,70–73).

It is notable that tenascin and fibrin, matrix proteins deposited in and around diseased (e.g., malignant tumors), or injured tissues (e.g., atherosclerotic lesions), or areas in which T-cells concentrate (40,43,55,57,59,63,70–73), and chemically modified matrix proteins (e.g., non-enzymatically glycated collagen IV [74]), all signal phagocytic leukocytes to become sessile. Dvorak et al. (70), and Singh et al. (59) have presented evidence that tumor stroma protects the tumors from host immune effector cells. Viewed from this perspective, tenascin contributes to an immunoinhibitory effect of tumor stroma.

$\beta_1$ integrins play no role in PMN or monocyte migration through Matrigel

Anti-$\beta_1$ integrins had no inhibitory effect on PMN or monocyte chemotaxis through Matrigel alone (FIGS. 17A and 17B), while antibodies directed against PMN and monocyte $\beta_2$ integrins blocked PMN and monocyte chemotaxis under all circumstances tested (75), including through Matrigel (FIGS. 17A and 17B). These findings suggest that $\beta_1$ integrins play no role in PMN or monocyte chemotaxis through Matrigel. These studies did not examine whether antibodies directed against $\beta_2$ integrins inhibited PMN or monocyte chemotaxis through Matrigel by blocking their adhesion to the Matrigel or by other mechanisms, such as stimulating an increase in their cAMP content (76).

On the mechanism(s) by which tenascin blocks PMN and monocyte chemotaxis

Chemoattractants that signal PMNs to remain sessile on fibrin gels, cause these cells to adhere more tightly and in greater numbers to fibrin than chemoattractants that promote PMN to migrate through fibrin gels. Similarly, chemoattractants stimulate monocytes to become sessile and adhere more tightly to glycated collagen IV than to native collagen IV (65,74). In contrast, no increase in the number of chemoattractant-stimulated PMN or monocytes that adhered to tenascin-impregnated Matrigel over Matrigel alone was observed. Thus, while fibrin and glycated matrices may inhibit chemotaxis by providing ligands to which chemoattractant-stimulated PMNs and monocytes bind very tightly, and in increased numbers, tenascin appears to exert its inhibitory effect by a different mechanism.

$\beta_1$ integrins have been reported to promote adhesion of normal and transformed cells to tenascin (53,54,60). F(ab)'$_2$ anti-tenascin, and anti-$\beta_1$ integrins reversed tenascin's inhibitory effect on both PMN and monocyte chemotaxis (FIGS. 17A and 17B). Since $\beta_1$ integrins appear to play no role in PMN or monocyte chemotaxis through Matrigel, the most straightforward explanation for the capacity of F(ab)'$_2$ anti-tenascin and anti-$\beta_1$ integrins to block tenascin's inhibitory effect on chemotaxis, is that the interaction of $\beta_1$ integrins on PMN and monocytes with cognate ligands on tenascin signals these cells to stop migrating.

The results of Example 1 show that $\beta_1$ integrins regulate the migration of fMLP-stimulated PMNs through fibrin and that antibodies or peptides that block $\beta_1$ integrins allow all PMNs to migrate through fibrin gel in response to chemoattractant that otherwise would cause PMNs to stop migrating when they encounter fibrin. Further work is needed to identify the cellular pathways via which $\beta_1$ integrins signal PMNs and monocytes to stop moving, and to determine the physiological significance of this event. Cellular pathways and physiological significance notwithstanding, one practical consequence of these findings is that antibodies vs PMN and monocyte $\beta_1$ integrins may be therapeutically useful by facilitating entry of these cells into tissues and body compartments from which they otherwise are excluded.

Tenascin has domains (53), which are homologous to regions in epidermal growth factor, fibronectin, and fibrinogen. Since fibrin and tenascin block monocyte and PMN migration, tenascin's fibrinogen-like terminal knob may play a critical role in signalling leukocytes to stop migrating.

References

1. Rot, A. (1991). The role of leukocyte chemotaxis in inflammation. In Biochemistry of Inflammation S. W. Evans and J. T. Whicher, eds). Kluwer Academic Publishers, Lancaster, 39–54.
2. Miller, M. D., and Krangel, M. S. (1992). Biology and biochemistry of the chemokines: a family of chemotactic and inflammatory cytokines. Crit. Rev. Immunol. 12:17–46.
3. Snyderman, R., and Uhing, R. J. (1992). Chemoattractant stimulus-response coupling. In Inflammation: basic principles and clinical correlates. J. I. Gallin, I. M. Goldstein, and R. Snyderman, eds. Raven Press, New York. 421–439.
4. Kishimoto, T. K., and Anderson, D. C. (1992). The role of integrins in inflammation. In Inflammation: basic principles and clinical correlates. J. I. Gallin, I. M. Goldstein, and R. Snyderman, eds. Raven Press, New York. 353–406.
5. Lasky, L. A., and Rosen S. D. (1992). The selectins. Carbohydrate binding adhesion molecules of the immune system. In Inflammation: basic principles and clinical correlates. J. I. Gallin, I. M. Goldstein, and R. Snyderman, eds. Raven Press, New York. 407–420.
6. Downey, G. P. (1994). Mechanisms of leukocyte motility and chemotaxis. Current Opinion in Immunol. 6:113–124.
7. Loike, J. D., Sodeik, B., Cao, L., Leucona, S., Weitz, J. I., Detmers, P. A., Wright, S. D., and Silverstein, S. C. (1991). CD11c/CD18 on Neutrophils recognizes a domain at the N terminus of the A$\alpha$ of fibrinogen. Proc. Natl. Acad. Sci, 88:1044–1048.
8. Loike, J. D., Silverstein, R., Wright, S. D., Weitz, J. I., and Silverstein, S. C. (1992). The role of protected extracellular compartments in interactions between leukocytes, and platelets and fibrin/fibrinogen matrices. In Plasminogen activation in fibrinolysis, in tissue remodeling, and in development. P. Brakman, and C. Kluft. Editors. Ann. N.Y. Acad. Sci. 667:163–172.
9. Wright, S. D., Weitz, J. I., Huang, A. J., Levin, J. M., Silverstein, S. C., and Loike, J. D. (1988). Complement receptor type three (CD11b/CD18) of human polymorphonuclear leukocytes recognizes fibrinogen. Proc. Natl. Acad. Sci. 85,7734–7738.
10. Loike, J. D., Silverstein, R., Cao, L., Solomon, L., Weitz, J. I., Haber, E., Matsueda, G. R., Bernatowicz, M. S., and Silverstein, S. C. (1993). Activated platelets form protected zones of adhesion with fibrinogen and fibronectin-coated surfaces. J. Cell Biol. 121:945–955.
11. Smith, W. B., Gamble, J. R., Clark-Lewis, I., and Vadas, M. A. (1993). Chemotactic desensitization of neutrophils demonstrates IL 8 dependent and IL-8 independent mechanisms of transmigration through cytokine activated endothelium. Immunology 78:491–497.
12. Zigmond, S. H., and Hirsch, J. G. (1973). Leukocyte locomotion and chemotaxis. New methods for evaluation, and demonstration of a cell derived chemotactic factor. J. Exp. Med. 137, 387–410.
13. Harvath L., and Leonard, E. J. (1982). Two neutrophil populations in human blood with different chemotactic activities: separation and chemoattractant binding. Infect. Immunol. 36:443–449.
14. Furie M. B., Naperstek, B. L., and Silverstein, S. C. (1987). Migration of neutrophils across monolayers of cultured microvascular endothelial cells. An in vitro model of leucocyte extravasation. J. Cell. Sci. 88:161–175.
15. Weston, S. A. and Parish, C. R. (1990). New fluorescent dyes for lymphocyte migration studies. Analysis by flow cytometry and fluorescence microscopy. J. Immunol. Meth. 133:87–97.
16. Howlett, A. R., Bissell, M. J. (1993). The influence of tissue microenvironment (stroma and extracellular matrix) on the development and function of mammary epithelium. Epithelila Cell Biol. 2:79–89.
17. Klemke, R. L., Yebra, M., Bayna, E. M., and Cheresh, D. A. (1994). $\alpha v \beta 5$ directed cell mobility but not adhesion on vitronectin. J. Cell Biol. 127:859–866.
18. Milici, A. J., Furie, M. B., and Carly, W. W. (1985). The formation of fenestration and channels by capillary endothelium in vitro. Proc. Natl. Acad. Sci. 82:6181–6185.

19. Calof A. L., and Lander, A. D. (1991). Relationship between neuronal migration and cell-substratum adhesion: laminin and merosin promote olfactory neuronal migration but are anti-adhesive. J. Cell Biol. 115:779–794.
20. Bronner-Fraser, M. (1994). Neural crest cell formation and migration in the developing embryo. FASEB J. 8:699–706.
21. Detmers, P. A., Lo, S. K., Olsen-Egbert, E., Walz, A., Baggiolini, M., and Cohn, Z. A. (1990). Neutrophil-activating protein 1/interleukin 8 stimulates the binding activity of the leukocyte adhesion receptor CD11b/CD18 on human neutrophils. J. Exp. Med. 171, 1155–1162.
22. Lundgren-Akerlund, E., Berger, E., and Arfors, K. E. (1992). Effect of divalent cations on adhesion of PMNs to matrix molecules in vitro. J. Leuk. Biol. 51:603–608.
23. Thompson, H. L., and Matsushima, K. (1992). Human polymorphonuclear leucocytes stimulated by TNF-$\alpha$ show increased adherence to extracellular matrix proteins which is mediated via the CD11b/18 complex. Clin. Exp. Immunol. 90:280–285.
24. Pommier C. G., Inada, S., Fries, L. F. Takahashi, T., Frank, M. M., and Brown, E. J. (1983). Plasma fibronectin enhances phagocytosis of opsonized particles by human peripheral blood monocytes. J. Exp. Med. 157:1844–1854.
25. Wright, S. D., Licht, M. R., Craigmyle, L. S., and Silverstein, S. C. (1985). Communication between receptors for different ligands on a single cell: ligation of fibronectin receptors induces a reversible alteration in the function of complement receptors on cultured human monocytes. J. Cell Biol. 99:336–339.
26. Monboisse, J. C., Bellon, G., Randoux, A., Duffer, J., and Borel, J. P. (1990). Biochem. J. 270:459–462.
27. Monboisse, J-C., Garnotel, R., Bellon, G., Ohno, N., Perreau, C., Borel J. P., and Kefalides. (1994). The $\alpha 3$ chain of type IV collagen prevents activation of human polymorphonuclear leukocytes. J. Biol. Chem. 269:25475–25482.
28. Nicosia, R. F. and Tuszynski, G. P. (1994). Matrix-bound thrombospondin promotes angiogenesis in vitro. J. Cell Biol. 124:183–193.
29. Ohno, K., and Maier., P. (1994). Cultured rat hepatocytes adapt their cellular glycolytic activity and adenylate energy status to tissue oxygen tension: influences of extracellular matrix components, insulin and glucagon. J. Cell. Physiol. 160:358–366.
30. Fuortes, M., Jen, W-W., and Nathan, C. (1993). Adhesion-dependent Protein Tyrosine Phosphorylation in Neutrophils Treated with Tumor Necrosis Factor J. Cell Biology 120:777–784.
31. DiMilla, P. A., Stone, J. A., Quinn, J. A., Albelda, S. M., and Lauffenburger, D. A. (1993). Maximal migration of human smooth muscle cells on fibronectin and type IV collagen occurs at an intermediate attachment strength. J. Cell Biol. 122:729–737.
32. Goodman, S. L., Risse, G., and von der Mark, K. (1989). The E8 subfragment of laminin promotes locomotion of myoblasts over extracellular matrix. J. Cell Biol. 109:799–809.
33. Weitz, J. I., Huang, A. J., Landman, S. L., Nicholson, S. C., and Silverstein, S. C. (1987). Elastase-mediated fibrinogenolysis by chemoattractant-stimulated neutrophils occurs in the presence of physiological concentrations of antiproteinases. J. Exp. Med. 166:1836–1850.
34. Lanir, N., Ciano, P. S., Van De Water, L., McDonagh, J., Dvorak, A. N., and Dvorak, H. P. (1988). Macrophage migration in fibrin gel matrices. II. Effects of clotting factor XIII, fibronectin, and glycosaminoglycan content on cell migration. J. Immunol. 140:2340–2349.
35. Campbell, E. J., Senior, R. M., McDonald, J. A., and Cox, D. L. (1982). Proteolysis by neutrophils. Relative importance of cell-substrate contact and oxidative inactivation of proteinase inhibitors in vitro. J. Clin. Invest. 70:845–852.
36. Huhtala, P., Humpries, M., McCarthy, J., Werb Z., and Damsky, C. (1994). The RGD and CS-1 containing cell binding regions of fibronectin signal opposing effects on metalloproteinase expression via $\alpha 5\beta 1$. Mol. Biol. Cell 5:64a.
37. Balsamo J, Ernst H, Zanin M K B, Hoffman S, Lilien J. (1995). The interaction of the retina cell surface N-acetylgalactosaminylphosphotransferase with an endogenous proteoglycan ligand results in inhibition of cadherin-mediated adhesion, J. Cell Biol, 129:1391–1401.
38. Bourdon, M. A., Ruoslahti, E. (1989). Tenascin mediates cell attachment through an RGD-dependent receptor. J. Cell Biology 108:1149–1155.
39. Boyum, A., Lovhaug, D., Tresland, L., Nordlie, E. M. (1991). Separation of leucocytes: improved cell purity by fine adjustments of gradient medium density and osmolality. Scand. J. Immunol. 34:697–712.
40. Chilosi, M., Lestani, M., Benedetti, A., Montagna, L., Pedron, S., Scarpa, A., Menestrina, F., Hirohashi, S., Pizzolo, G., and Semenzato, G. (1993). Constitutive expression of tenascin in T-dependent zones of human lymphoid tissues. Am. J. of Path. 143:1348–55.
41. Chiquet-Ehrismann, R. (1993). Tenascin and other adhesion-modulating proteins in cancer.[Review]. Sem. in Cancer Biol. 4:301–10.
42. Chuong, C. M., and Chen, H. M. (1991). Enhanced expression of neural cell adhesion molecules and tenascin (tenascin) during wound healing. Am. J. Pathol. 138:427–440.
43. Erickson, H. P. and Bourdon, M. A. (1989). Tenascin: an extracellular matrix protein prominent in specialized embryonic tissues and tumors. Ann. Rev. Cell. Biol. 5:71–92.
44. Grumet, M., Hoffman, S. Crossin, K. L., and Edelman, G. M. (1985). Tenascin, an extracellular matrix protein of neural and non-neural tissues that mediates glial-neuron interaction. Proc. Natl. Aca. Sci. 82:8075–9079.
45. Herlyn, M., Graeven, U., Speicher, D., Sela, B. A., Bennicelli, J. L., Kath, R., Guerry, D. (1991). Characterization of tenascin secreted by human melanoma cells. Cancer Res. 51:4853–8.
46. Hoffman, S., Crossin, K. L., and Edelman, G. M. (1988). Molecular forms, binding functions, and developmental expression patterns of cytotactin and cytotactin-binding proteoglycans, an interactive pair of extracellular matrix molecules. J. Cell Biol. 106:519–532.
47. Hoffman, S. Dutton, S. L., Ernst, H., Boackle, M. K., Everman, D., Tourkin, A., and Loike, J. D. (1994). Func- 48. Joshi, P., Chung, C. Y., Aukhil, I., and Erickson, H. P. (1993). Endothelial cells adhere to the RGD domain and the fibrinogen-like terminal knob of tenascin. J. Cell Sci. 106:389–400.
49. Juhasz, I., Murphy, G. F., Yan, H. C., Herlyn, M., Albelda, S. M. (1993). Regulation of extracellular matrix proteins and integrin cell substratum adhesion receptors on epithelium during cutaneous human wound healing in vivo. Am. J. of Path. 143:1458–69.
50. Mackie., E. J., Halfter, W., and Liverani, D. (1988). J. Cell Biol. 107:2757–2767.
51. Mackie, E. J., Chiquet-Ehrismann, R., Pearson, C. A., Inaguma, Y. M., Taya, K., Kawarada, Y., and Sakakura, T. (1987). Proc. Natl. Acad. Sci., 84:4621–4625.
52. Pesheva, P., Probstmeier, R., Skubitz, A. P., McCarthy, J. B., Furcht, L. T. and Schachner, M. (1994). Tenascin-R J1 160/180 inhibits fibronectin-mediated cell adhesion—functional relatedness to tenascin-C. J. Cell Sci. 107:2323–33.
53. Prieto, A. L., Andersson-Fisone, C. and Crossin, K. L. (1992). Characterization of multiple adhesive and counteradhesive domains in the extracellular matrix protein cytotactin. J. Cell Bio. 119:663–78.
54. Prieto, A. L., Edelman, G. M., and Crossin, K. L. (1993). Multiple integrins mediate cell attachment to cytotactin/tenascin. Proc. Natl. Acad. Sci. USA 90:10154–8.
55. Ruegg, C. R., Chiquet-Ehrismann, R., and Alkan, S. S. (1989). Tenascin, an extracellular matrix protein, exerts immunomodulatroy activities. Proc. Natl. Acad. Sci. 86:7637–7441.
56. Sakai, T., Kawakatsu, H., Hirota, N., Yokoyama, T., Sakakura, T., and Saito, M. (1993). Specific expression of tenascin in human colonic neoplasms. British Journal of Cancer 67:1058–64.
57. Sharifi, B. G., D. W. Lafleur, S. M. Schwartz, J. S. Forrester, J. A., Fagin. (1995). Expression of tenascin isoforms are selectively up-regulated following aortic balloon injury. The FASEB Journal, 9: a611.
58. Shoji, T., Kamiya, T., Tsubura, A., Hatano, T., Sakakura, T., Yamamoto, M., Morii, S. (1992). Immunohistochemical staining patterns of tenascin in invasive breast carcinomas. Virchows. Arch. A. Pathol. Anat. Histopathol. 421:53–6.
59. Singh, S., Ross, S. R., Acena, M., Rowly, D. A., and Schreiber, H. (1992). Stroma is critical for preventing or permitting immunological destruction of antigenic cancer cells. J. Exp. Med. 175:139–146.
60. Sriramarao, P., Mendler, M., and Bourdon, M. A. (1993). Endothelial cell attachment and spreading on human tenascin is mediated by alpha 2 beta 1 and alpha v beta 3 integrins. J. Cell Sci. 105:1001–12.
61. Tourkin A., Anderson T., LeRoy EC, Hoffman S. (1993). Eosinophil adhesion and maturation is modulated by laminin. Cell Adhesion and Communication, 1:161–176.
62. Wehrle-Haller, B. and Chiquet, M. (1993). Dual function of tenascin: simultaneous promotion of neurite growth and inhibition of glial migration. J. Cell Sci. 106:597–610.
63. Hiraiwa, N., Kida, H., Sakakura, T., and Kusakabe, M. (1993). Induction of tenascin in cancer cells by interactions with embryonic mesenchyme-mediated by a diffusible factor. J. Cell. Sci. 104:289.
64. Koukouus, G. K., Gould, V. E., Bhattacharyya, A., Gould, J. E., Howeedy, A. A., and Virtanen, I. (1991). Tenascin in normal, reactive, hyperplastic and neoplastic tissue: biological and pathological implications. Hum. Pathol. 22:636.
65. El Khoury, J., Loike, J., Cao, L., Thomas, C. and Silverstein, S. C. (1994). Macrophages adhere to glucose-modified basement membrane collagen via their scavenger receptors. J. Biol. Chem. 269:10197–10200.
66. Loike, J. D., Somes, M., and Silverstein, S. C. (1986). Creatine uptake, metabolism, and efflux in human monocytes and macrophages. Am. J. Physiol. 251:C128.
67. Friedlander, D. R., Hoffman, S., and Edelman, G. M. (1988). Functional mapping of cytotactin: proteolytic fragments active in cell-substrate adhesion. J. Cell Biol. 107:2329.
68. Lundgren-Akerlund, E., Olofsson, A. M., Bergerand, E., and Arfors, K. E. (1993). CD11b/CD18-dependent polymorphonuclear leucocyte interaction with matrix proteins in adhesion and migration. Scan. J. Immunol. 37:569.
69. Islam, L. N., McKay, I. C., and Wilkinson, P. C. (1985). The use of collagen or fibrin gels for the assay of human neutrophil chemotaxis. J. Immunol. Meth. 85:137.
70. Dvorak, H. F. (1986). Tumors: Wounds that do not heal. Similarities between tumor stroma generation and wound healing. N. Engl. J. Med. 315:1650–1659.
71. Willhelm, O., Hafter, R., Coppenrath, E., Pflanz, M., Schmitt, M., Babic, R., Linke, R., Gossner, W., and Graeff, H. (1988). Fibrin-fibronectin compounds in Human ovarian tumor ascites and their possible relation to the tumor stroma. Can. Res. 48:3507.
72. Strickland D. K., Kounnas, M. Z., and Argraves, W. S. (1995). LDL receptor-related protein: a multiligand receptor for lipoprotein and proteinase catabolism. [Review] FASEB J. 9:890.
73. Costantini, V., Zacharski, L. R., Memoli, V. A., Kisiel, W., Kudryk, B. J., Rousseau, S. M., and Stump. D. C. (1992). TI-Fibrinogen deposition and macrophage-associated fibrin formation in malignant and nonmalignant lymphoid tissue. J. Lab. & Clin. Med. 119:124.
74. Schmidt A. M., Yan, S. D., Brett, J., Mora, R., Nowygrod, R., and Stern, D. (1993). Regulation of human mononuclear phagocyte migration by cell surface-binding proteins for advanced glycation end products. J. Clin. Invest. 91:2155.
75. Gao, J. X., Wilkins, J., and Issekutz, A. C. (1995). Migration of human polymorphonuclear leukocytes through a synovial fibroblast barrier is mediated by both beta 2 (CD11/CD18) integrins and the beta 1 (CD29) integrins VLA-5 and VLA-6. Cell. Immunol. 163:178.
76. Gresham, H. D., Graham, I. L., Anderson, D. C., and Brown, E. J. (1991). Leukocyte adhesion-deficient neutrophils fail to amplify phagocytic function in response to stimulation. Evidence for CD11b/CD18-dependent and -independent mechanisms of phagocytosis. J. Clin. Invest. 88:588.

What is claimed is:

1. A method of preventing a chronic infection from occurring due to the presence of bacterial cells on a surface of a foreign body in a subject, which consists essentially of coating the foreign body before placing it in the subject with a fibrinolytic agent capable of preventing the accumulation of fibrin on the surface of the foreign body so as to permit leukocyte cells to reach and kill any bacterial cells present on the surface of the foreign body and thereby prevent the chronic infection.

2. The method of claim 1, wherein the foreign body is a prosthetic device.

3. The method of claim 1, wherein the foreign body is a catheter.

4. The method of claim 1, wherein the foreign body is a suture.

5. The method of claim 1, wherein the subject is a mammal.

6. The method of claim 5, wherein the mammal is a human.

7. The method of claim 1, wherein the fibrinolytic agent is a plasminogen activator.

8. The method of claim 7, wherein the plasminogen activator is urokinase.

9. The method of claim 7, wherein the plasminogen activator is streptokinase.

10. The method of claim 7, wherein the plasminogen activator is tissue plasminogen activator.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly Arg Gly Asp Ser Pro
    1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Gly Arg Gly Glu Ser Pro
    1                   5